(12) United States Patent
Liu et al.

(10) Patent No.: US 8,742,167 B2
(45) Date of Patent: Jun. 3, 2014

(54) THERAPEUTIC FORMULATIONS BASED ON ASIATIC ACID AND SELECTED SALTS THEREOF

(75) Inventors: Ying Liu, Shanghai (CN); Quanhai Liu, Shanghai (CN); Yan Qin, Shanghai (CN); Tong Wu, Shanghai (CN); Zhiru Xu, Shanghai (CN); Min-yu Liu, Shanghai (CN); Fei Li, Shanghai (CN); Yan Li, Shanghai (CN); Michael J. Newman, San Diego, CA (US)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 437 days.

(21) Appl. No.: 12/811,477

(22) PCT Filed: Jan. 8, 2009

(86) PCT No.: PCT/US2009/030458
§ 371 (c)(1),
(2), (4) Date: Sep. 2, 2010

(87) PCT Pub. No.: WO2009/089365
PCT Pub. Date: Jul. 16, 2009

(65) Prior Publication Data
US 2010/0331413 A1 Dec. 30, 2010

Related U.S. Application Data

(60) Provisional application No. 61/006,432, filed on Jan. 11, 2008.

(51) Int. Cl.
*C07C 61/29* (2006.01)

(52) U.S. Cl.
USPC .......................................................... 562/510

(58) Field of Classification Search
CPC . C07C 2103/52; C07C 215/08; A61K 31/205
See application file for complete search history.

(56) References Cited

U.S. PATENT DOCUMENTS

| 3,366,669 | A | * | 1/1968 | Ratsimamanga et al. | .... 560/194 |
| 4,304,788 | A | * | 12/1981 | Edge et al. | .................... 514/532 |
| 6,891,063 | B1 | | 5/2005 | Mora et al. | |
| 2006/0106206 | A1 | | 5/2006 | Loiseau et al. | |
| 2007/0010459 | A1 | | 1/2007 | Liu et al. | |
| 2009/0253663 | A1 | * | 10/2009 | Akamatsu et al. | ............. 514/171 |

FOREIGN PATENT DOCUMENTS

| CN | 1347398 A | 5/2002 |
| EP | 0867447 | 9/1998 |
| EP | 0867447 A1 | 9/1998 |
| WO | WO9617819 A1 | 6/1996 |
| WO | WO9837899 A | 9/1998 |
| WO | WO0063148 A1 | 10/2000 |
| WO | WO02/17904 A1 | 3/2002 |

OTHER PUBLICATIONS

Aldrich, Handbook of Fine Chemicals and Laboratory Equipment, 2002, Milwaukee, WI, p. 1896.*
Iloprost Update: Treatment of pulmonary hypertension—current aspects, 2006, Schering AG, Berlin, pp. 1-4, recovered from internet at http://www.ventavis.com/html/pdf/iloprost_update/iloprost_update_03.pdf on Sep. 16, 2013.*
Written Opinion and International Search Report for PCT/US2009/030458 dated Jul. 8, 2009, 8 pages.
Thongnopnua, "High-performance liquid chromatographic determination of asiatic acid in human plasma", The Thai Journal of Pharmaceutical Sciences, Jan.-Jun. 2008, vol. 32, No. 1-2; pp. 10-16.
Pinhas et al., "Structure of Madecassic Acid, New Triterpene of *Centella asiatica* of Madegascar," Bulletin de Société Chimique de France 1967, No. 6, pp. 1890-1895 (Jan. 1, 1967) (6 pages).
Yun et al., "Inhibition of LPS-induced NO and $PGE_2$ production by Asiatic acid via NF-kB inactivation in RAW 264.7 macrophages: Possible involvement of the IKK and MAPK pathways", International Immunopharmacology (2008), vol. 8, pp. 431-441, Dec. 3, 2007 online publication date, (12 pages).
Jung et al., "Structure-Activity Relationships of Polyhydroxyursane-type Triterpenoids on the Cytoprotective and Anti-inflammatory Effects," Natural Product Sciences, vol. 13(1), pp. 33-39, Mar. 2007 (8 pages).
Du et al., "Preparation of Ursane Triterpenoids from *Centella asiatica* Using High Speed Countercurrent Chromatography with Step-Gradient Elution," Journal of Liquid Chromatography & Related Technologies, vol. 27, No. 14, pp. 2201-2215 (2004) (16 pages).
Search Report dated Sep. 6, 2012, for Chinese Patent Application No. 200980108867.6, with English translation attached, Applicant: Shang Hai Institute of Pharmaceutical Industry (3 pages).
Division Office Action dated Aug. 18, 2011, for Chinese Patent Application No. 200980108867.6, with English translation attached, Applicant: Shang Hai Institute of Pharmaceutical Industry (3 pages).
The First Office Action dated Nov. 28, 2011, for Chinese Patent Application No. 200980108867.6, with English translation attached, Applicant: Shang Hai Institute of Pharmaceutical Industry (9 pages).
The Second Office Action dated Sep. 27, 2012, for Chinese Patent Application No. 200980108867.6, with English translation attached, Applicant: Shang Hai Institute of Pharmaceutical Industry (7 pages).
Extended European Search Report dated Jul. 2, 2012, for European Patent Application No. 09700319.8, Applicant: Shang Hai Institute of Pharmaceutical Industry (12 pages).

* cited by examiner

*Primary Examiner* — Paul A Zucker
(74) *Attorney, Agent, or Firm* — McCracken & Frank LLC

(57) ABSTRACT

A highly pure asiaticoside and a pharmaceutical grade asiatic acid can be prepared, along with salts of asiatic acid, for use in formulating therapeutic compositions that are suitable for treating arthritis, psoriasis and other inflammatory diseases, as well as pulmonary fibrosis, diabetic nephropathy, and other fibrotic diseases.

1 Claim, 32 Drawing Sheets

Figure 1: Overlay of Asiatic Acid Starting Material and Salts Produced
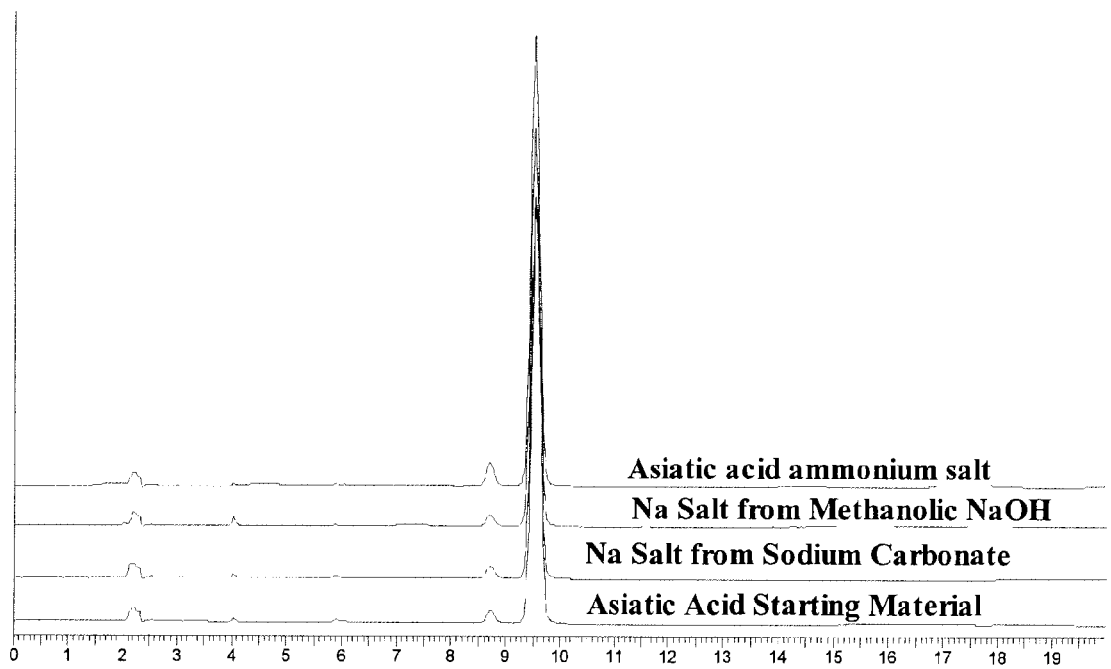

Figure 2: ¹H-NMR spectroscopic analysis in DMSO-$d_6$ of Asiatic Acid Lot 071109 and Sodium Salt AJF09,99b at 300 MHz
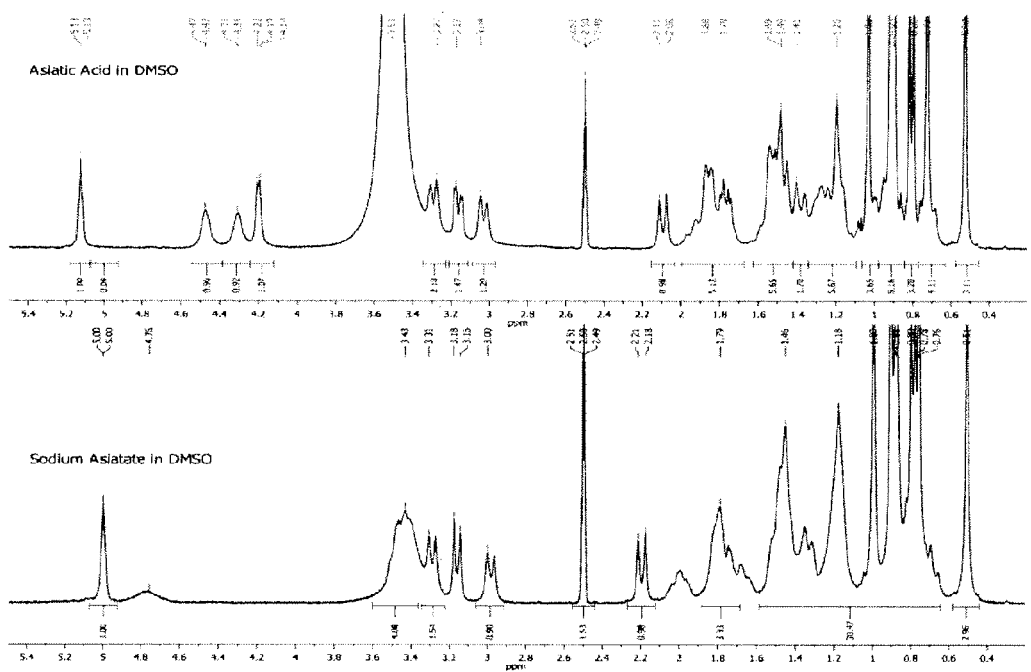

Figure 3: $^{13}$C-NMR spectroscopic analysis in DMSO-d$_6$ of Asiatic Acid Lot 071109 and Sodium Salt AJF09,99b at 300 MHz
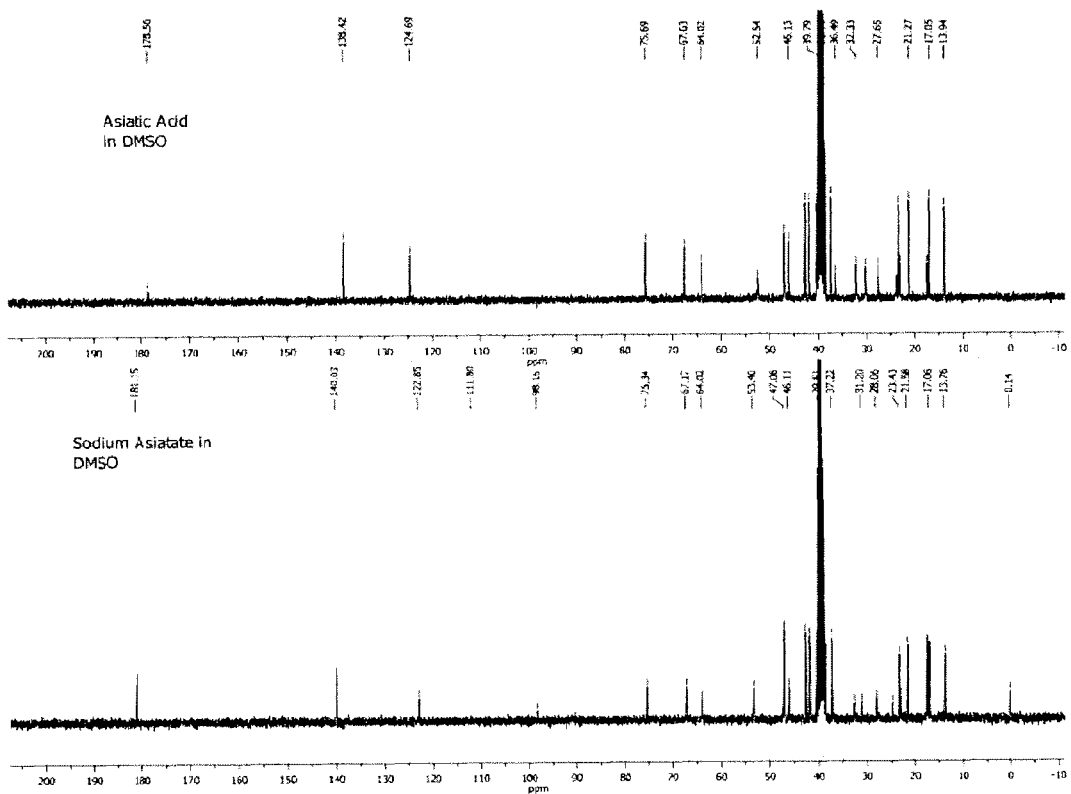

Figure 4. $^{13}$C-NMR spectroscopic analysis in DMSO-$d_6$ of Asiatic Acid and Sodium Salt AJF09,99b at 300 MHz (11 ppm – 41 ppm)
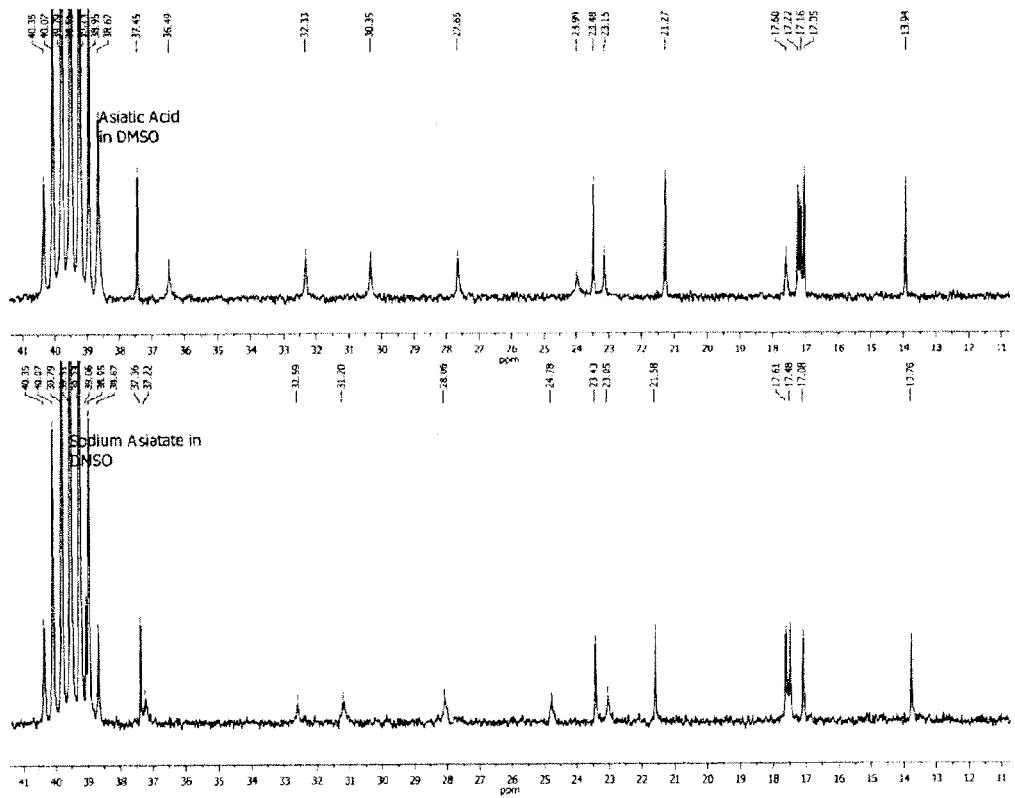

Figure 4a – complete $^1$H-NMR spectrum of Asiatic Acid in DMSO-d6
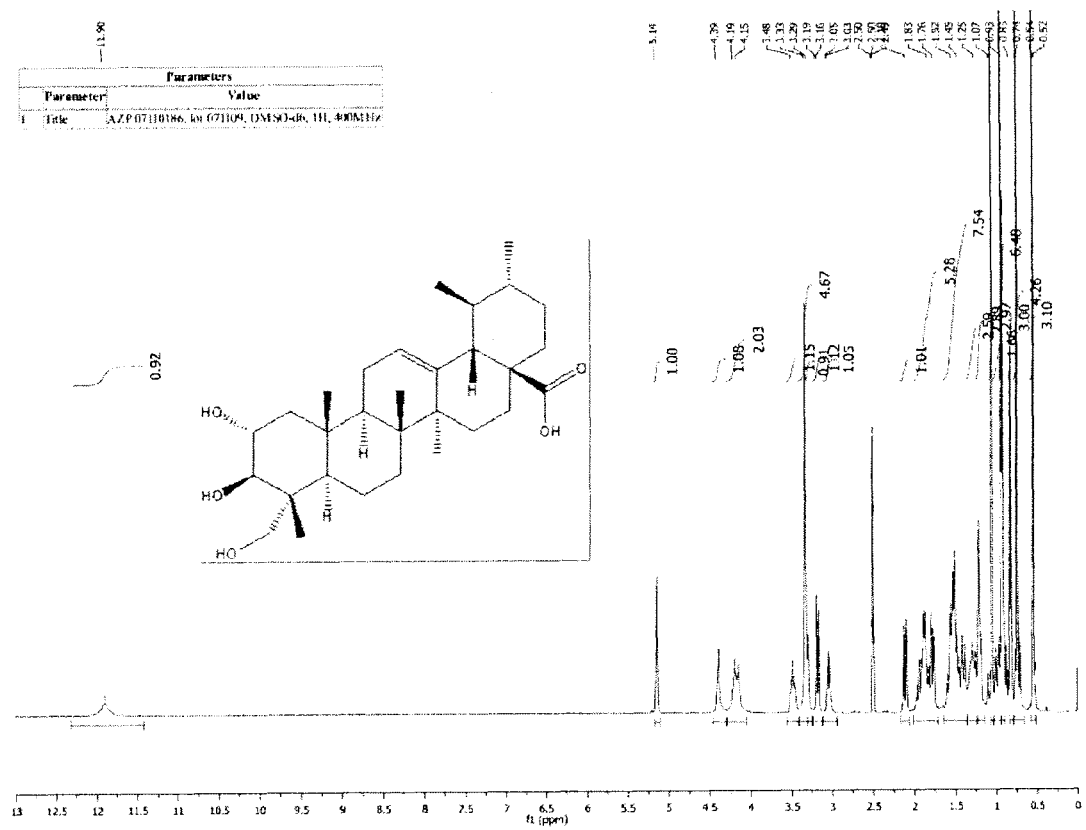

Figure 4b – Magnified view of Asiatic Acid ¹H-NMR spectrum
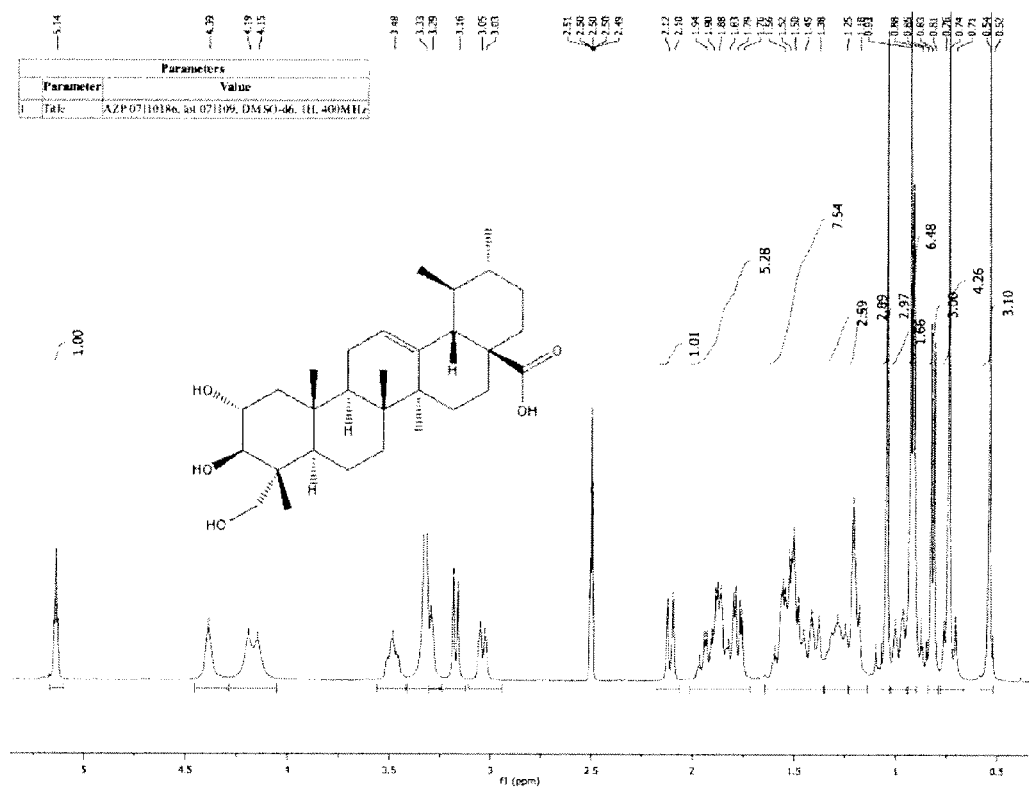

Figure 4c – Complete 1H-NMR spectrum of Asiatic Acid Sodium Salt (AJF09, 99b)
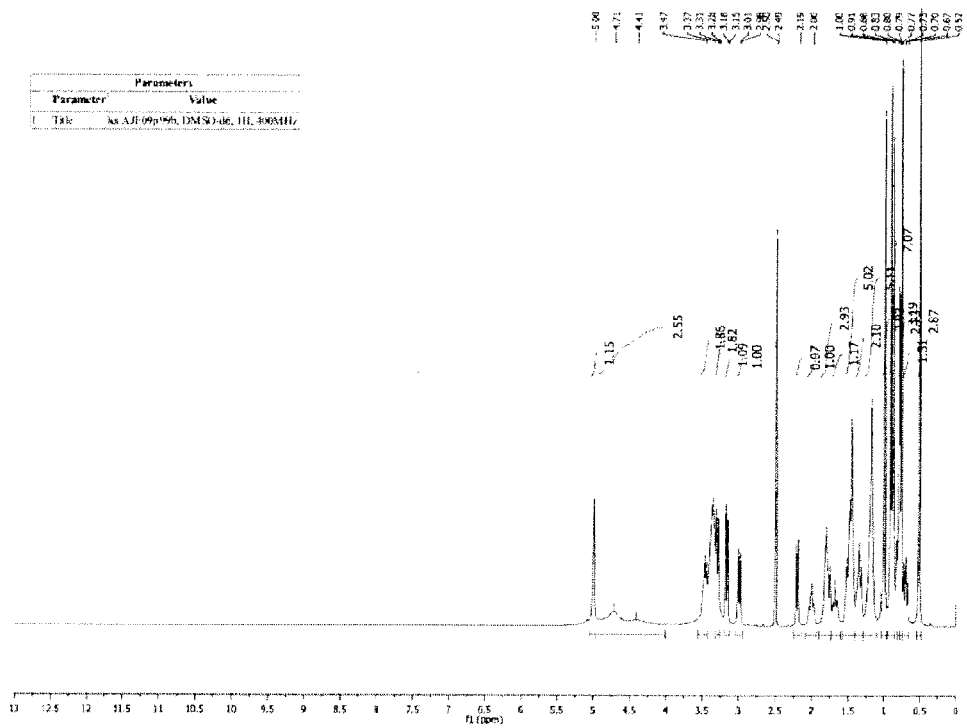

Figure 4d – Magnified view of Asiatic Acid Sodium salt $^1$H-NMR spectrum
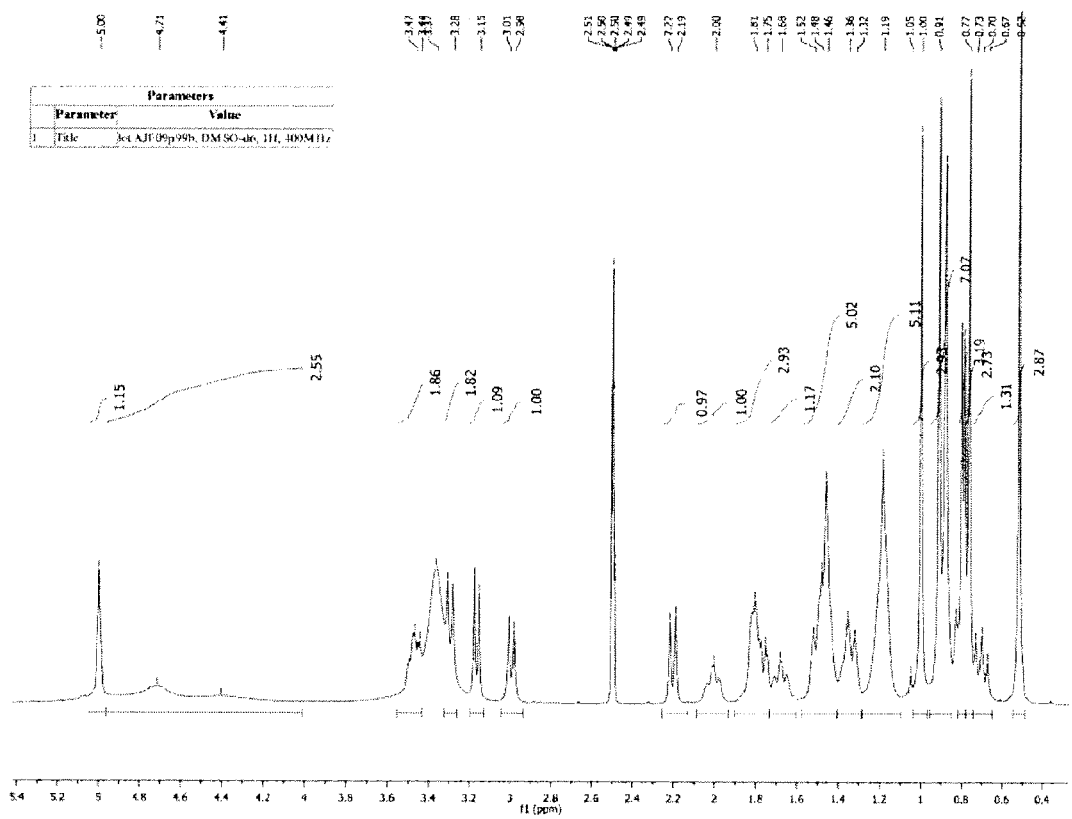

Figure 4e – Complete $^{13}$C-NMR spectrum of Asiatic Acid in DMSO-d$_6$
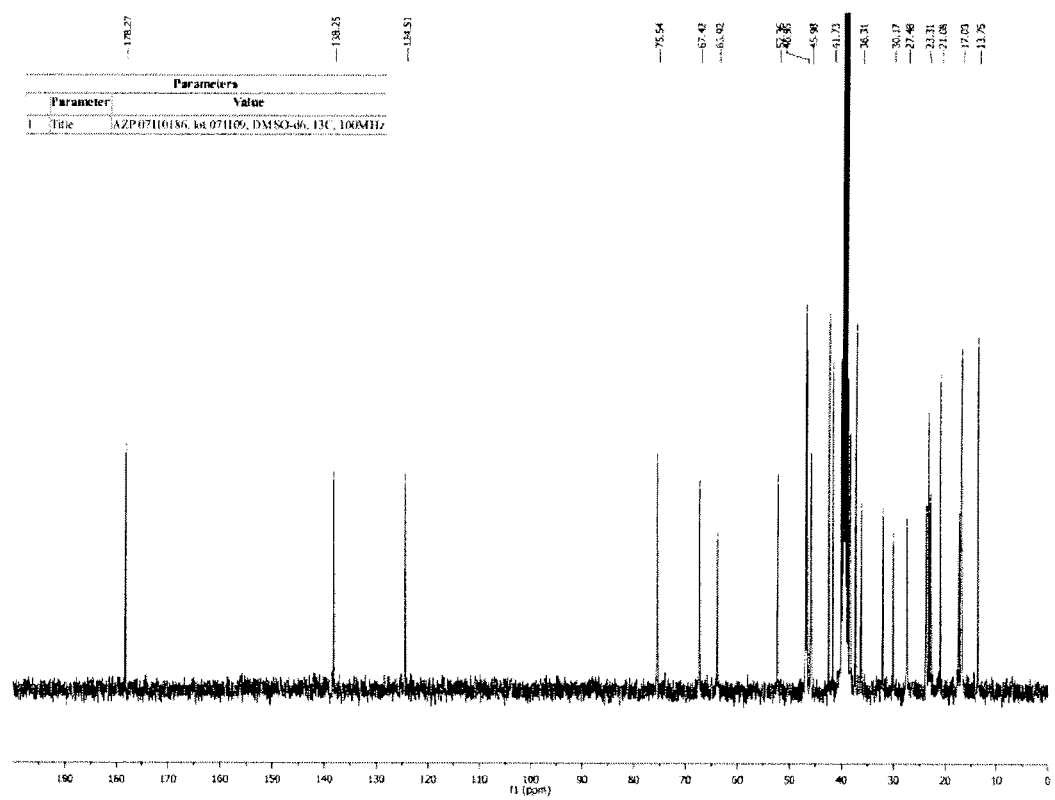

Figure 4f – Magnified view of Asiatic Acid 13C-NMR spectrum
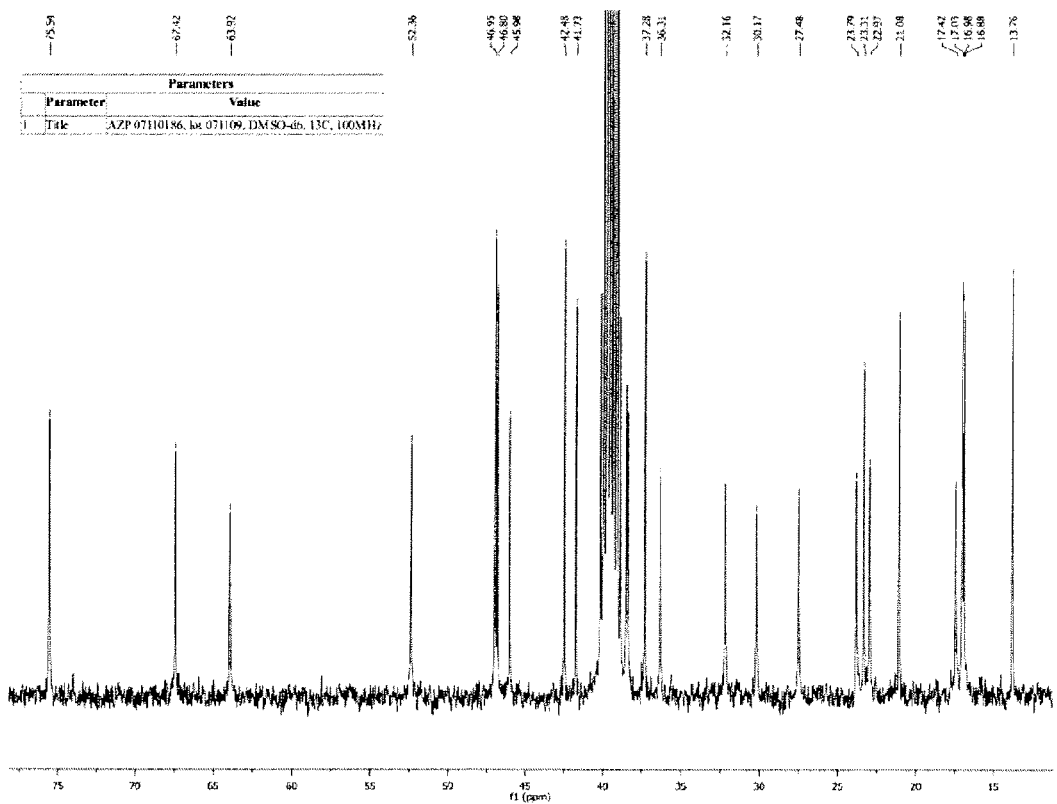

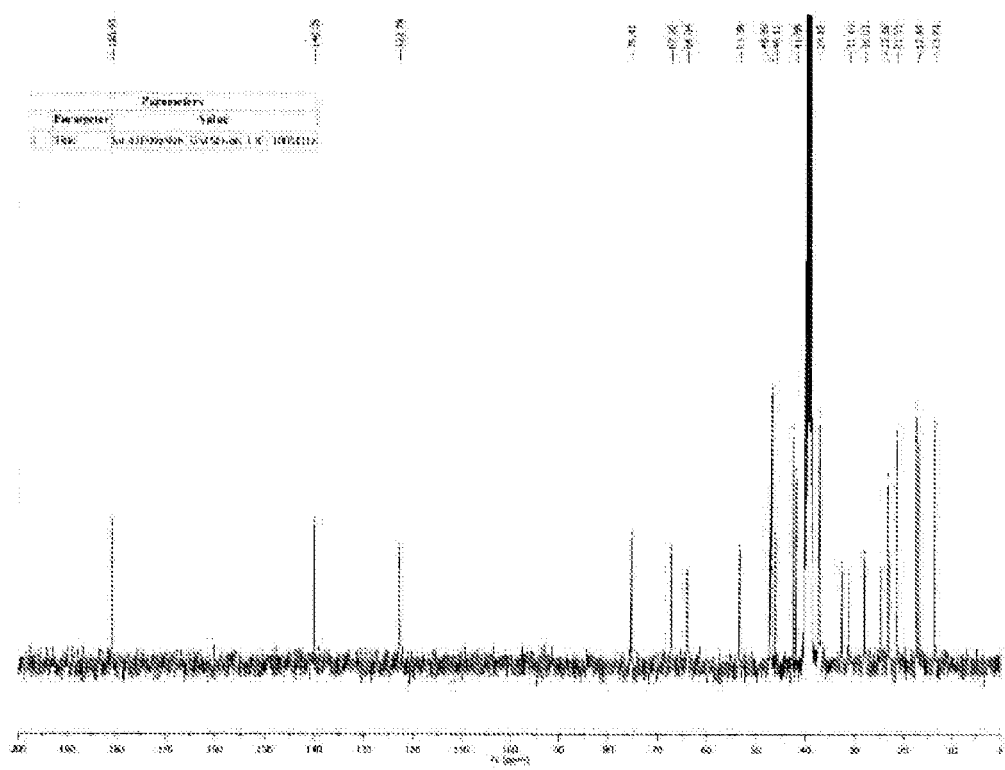
Figure 4g – Complete $^{13}$C-NMR spectrum of Asiatic Acid Sodium Salt in DMSO-$d_6$ Figure 4h – Magnified view of Asiatic Acid Sodium Salt $^{13}$C-NMR spectrum
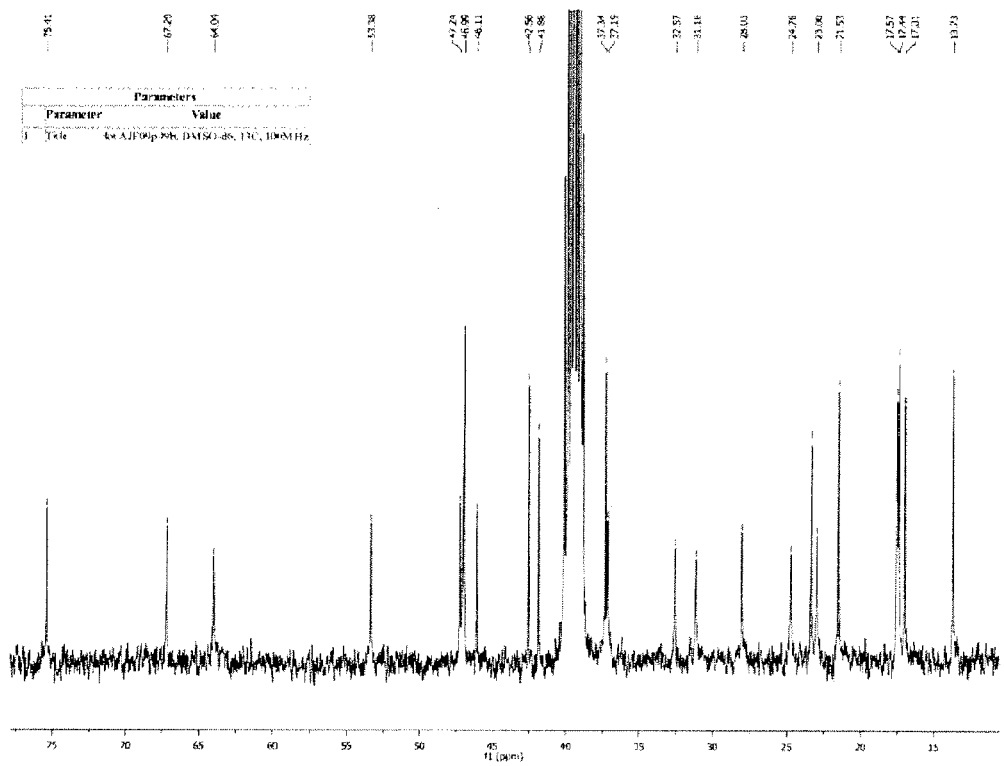

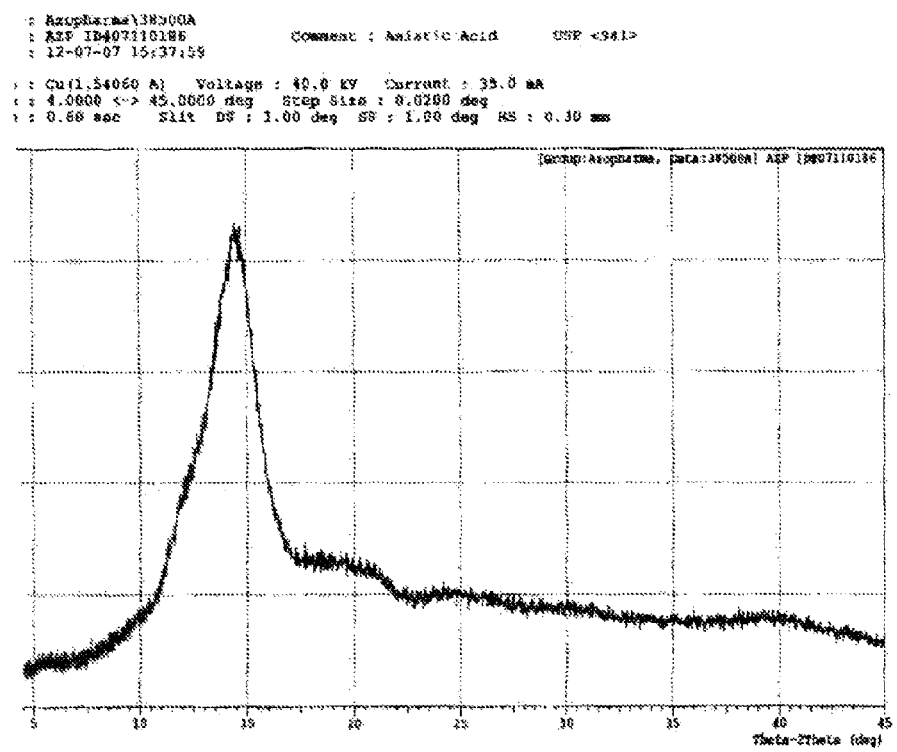
Figure 5a: PXRD of Asiatic Acid

Figure 5b: PXRD of Sodium Salt of Asiatic Acid
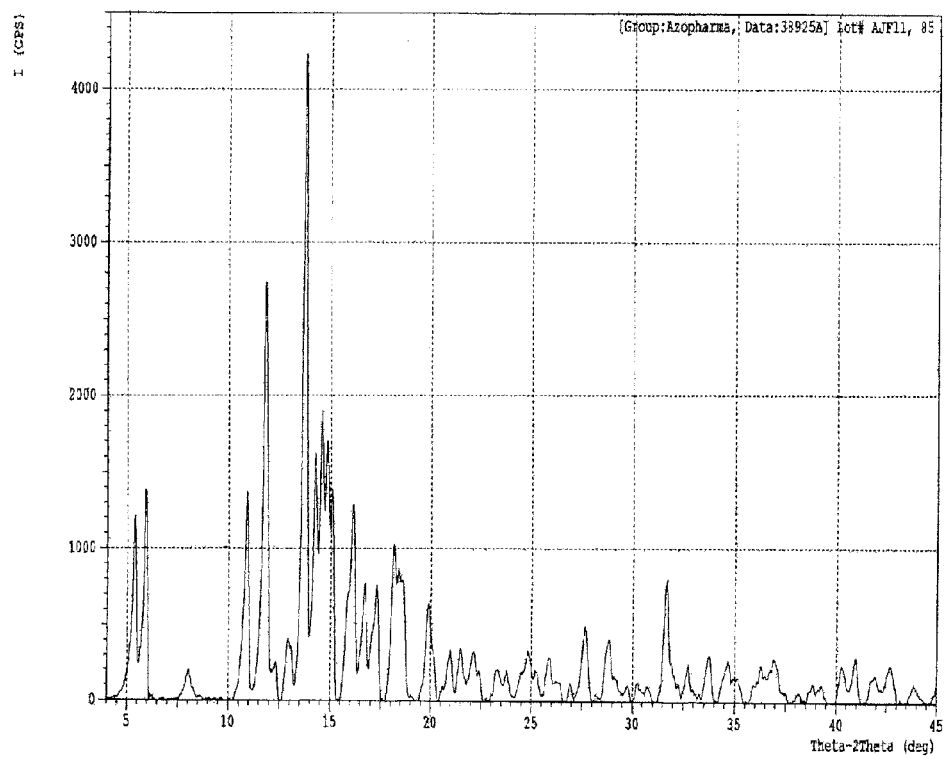

Figure 6: FTIR Spectrum of Asiatic Acid
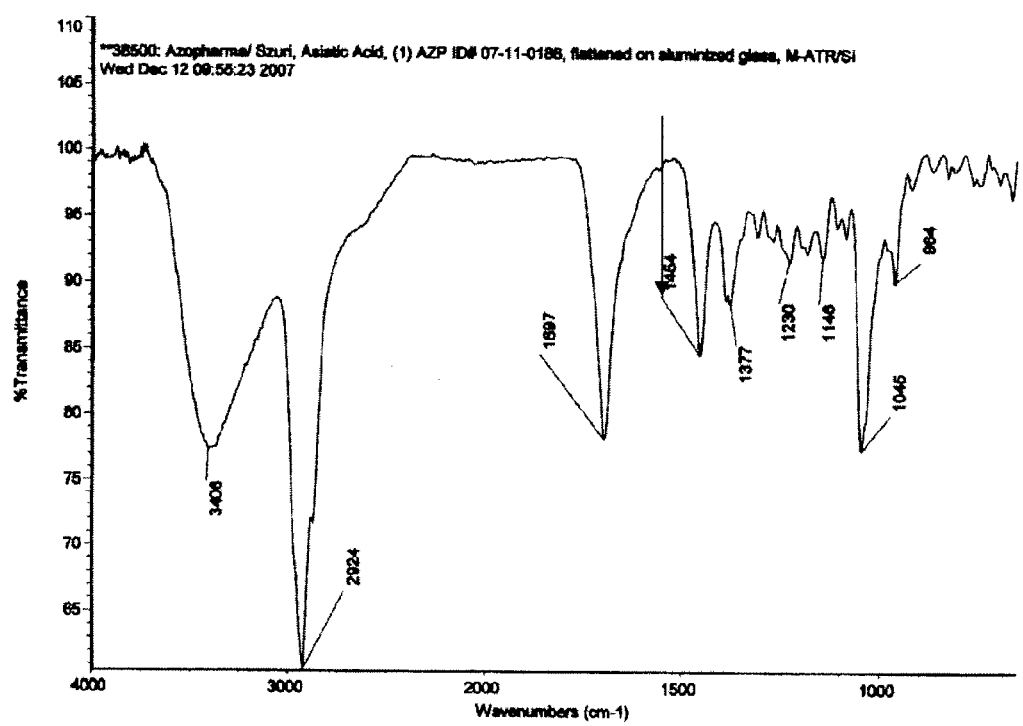

Figure 7: FTIR Spectrum of Asiatic Acid Sodium Salt AJF09,82
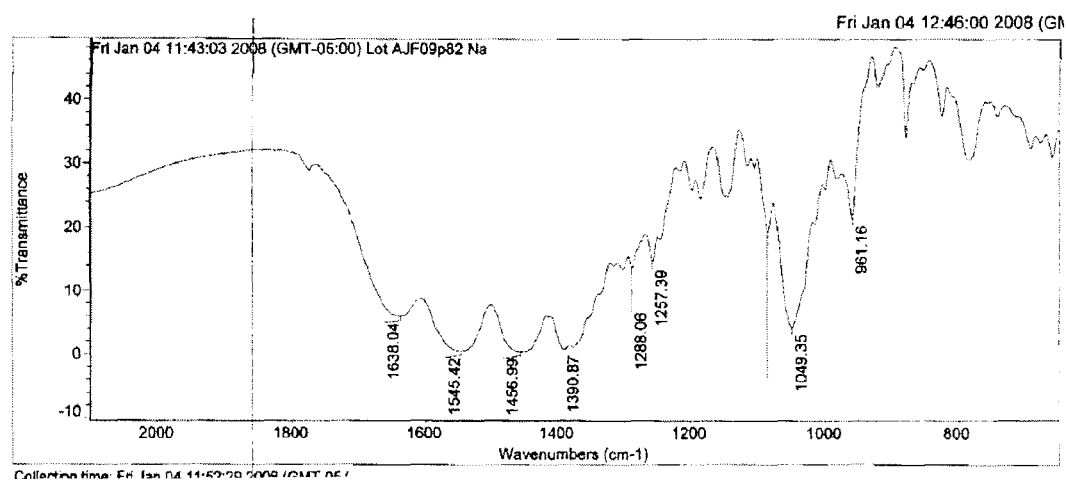

Figure 8: FTIR Spectrum of Asiatic Acid Sodium Salt AJF09,99b
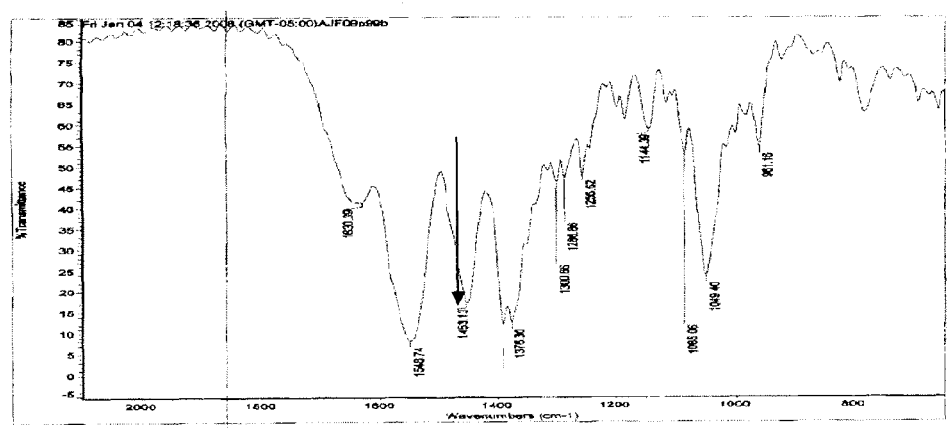

Figure 9: FTIR Spectrum of Asiatic Acid Ammonium Salt AJF09,99a
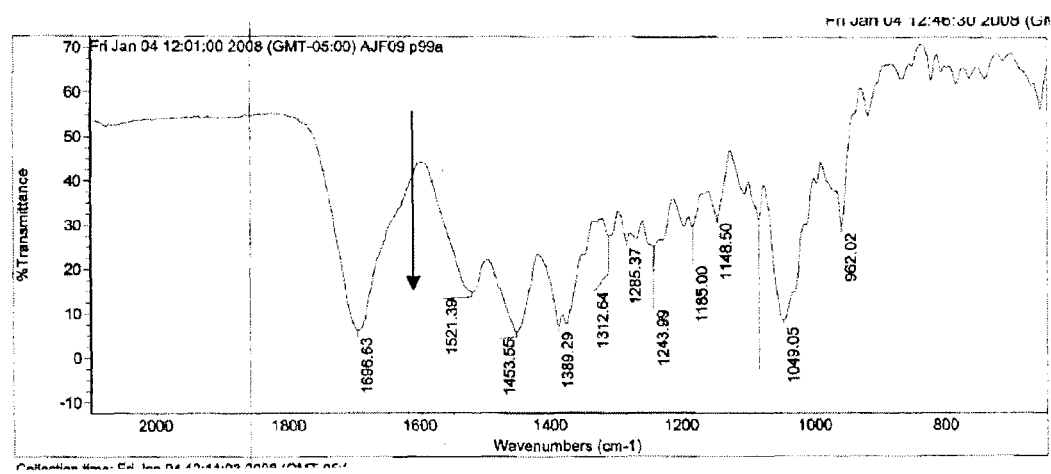

Figure 10: TGA Thermogram of Asiatic Acid Lot 071109
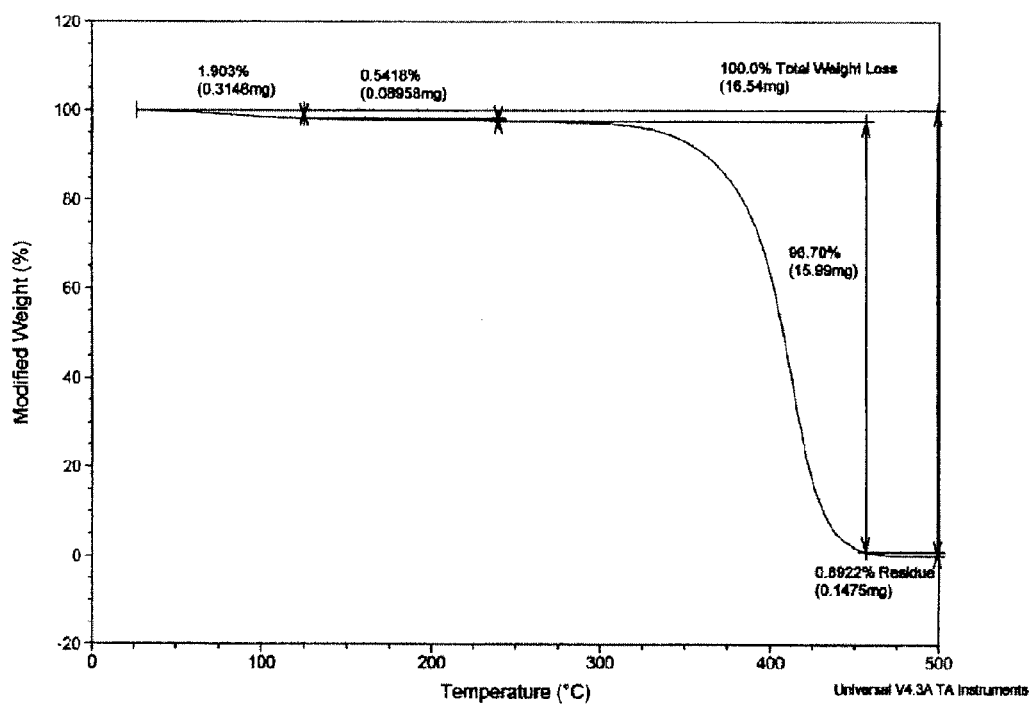

Figure 11: TGA Thermogram of Asiatic Acid Sodium Salt AJF09,82
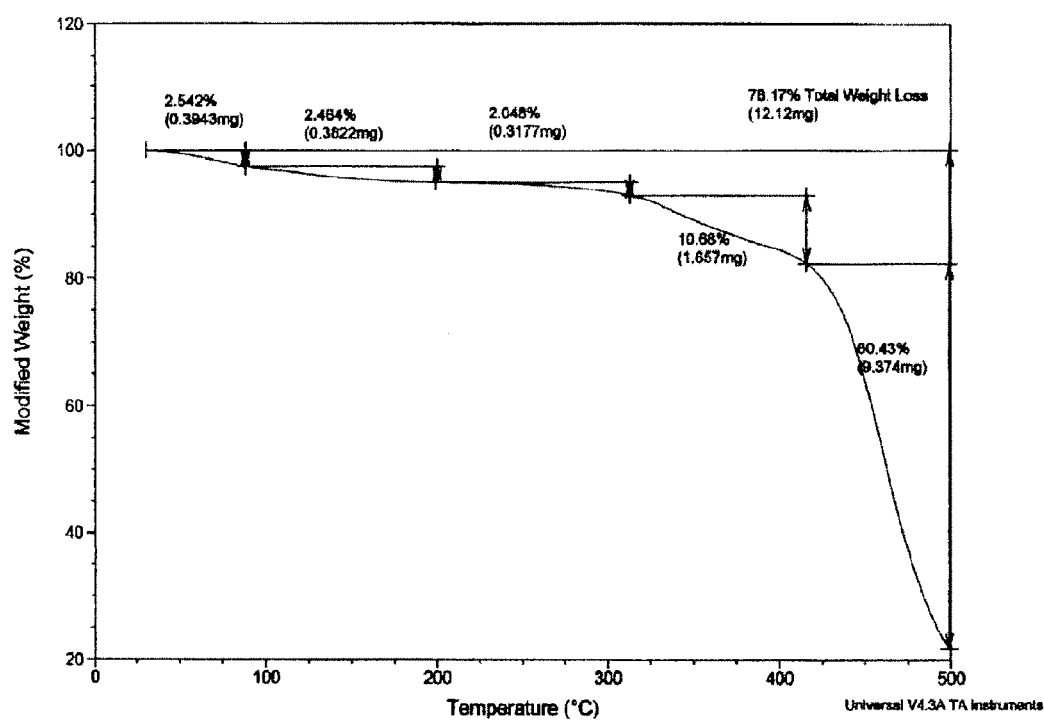

Figure 12: TGA Thermogram of Asiatic Acid Sodium Salt AJF09,99b
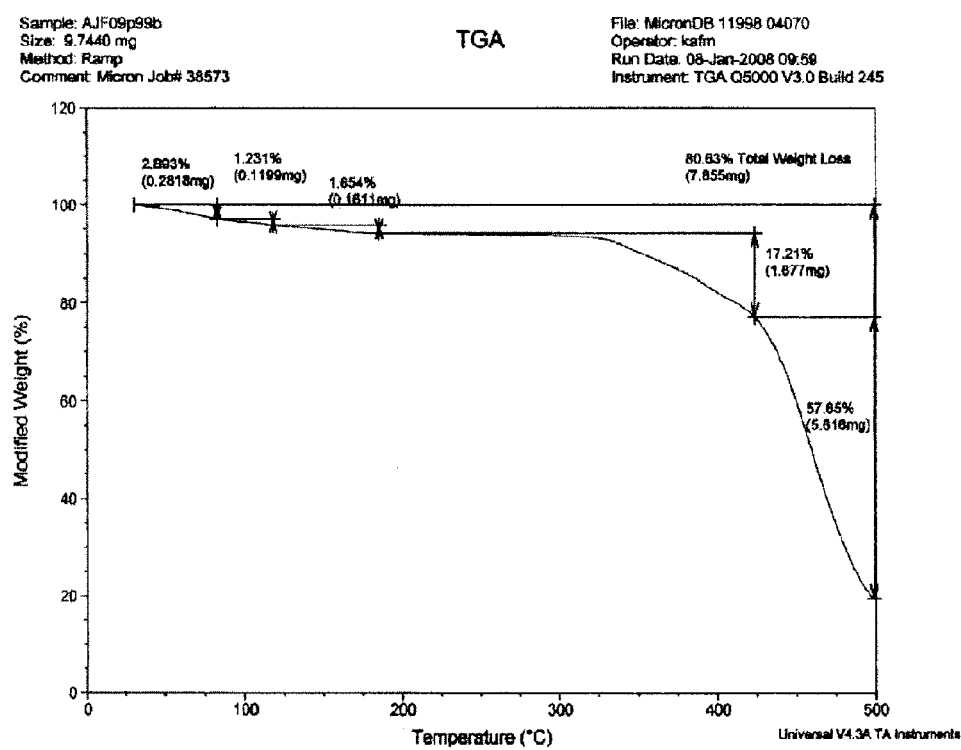

Figure 13: Standard Linearity Curve
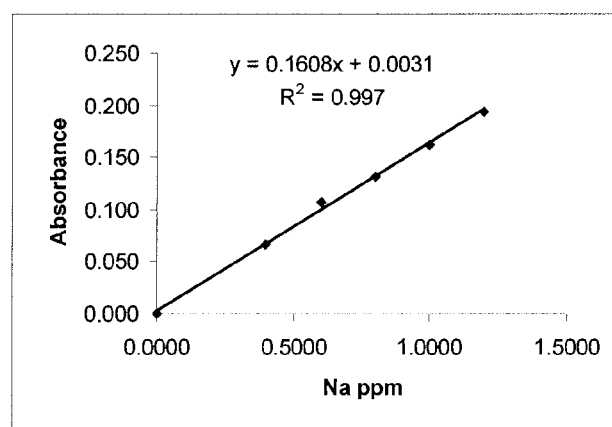

Figure 14:   Summary of Process for Asiaticoside Production
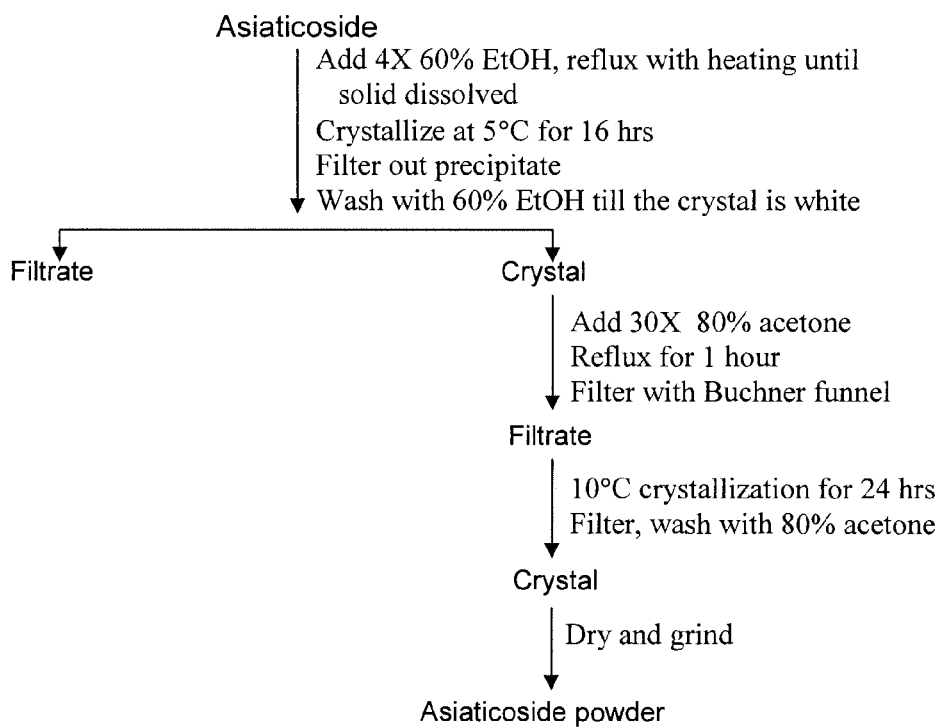

Figure 15: Summary of Process for Producing Pharmaceutical Grade Asiatic Acid
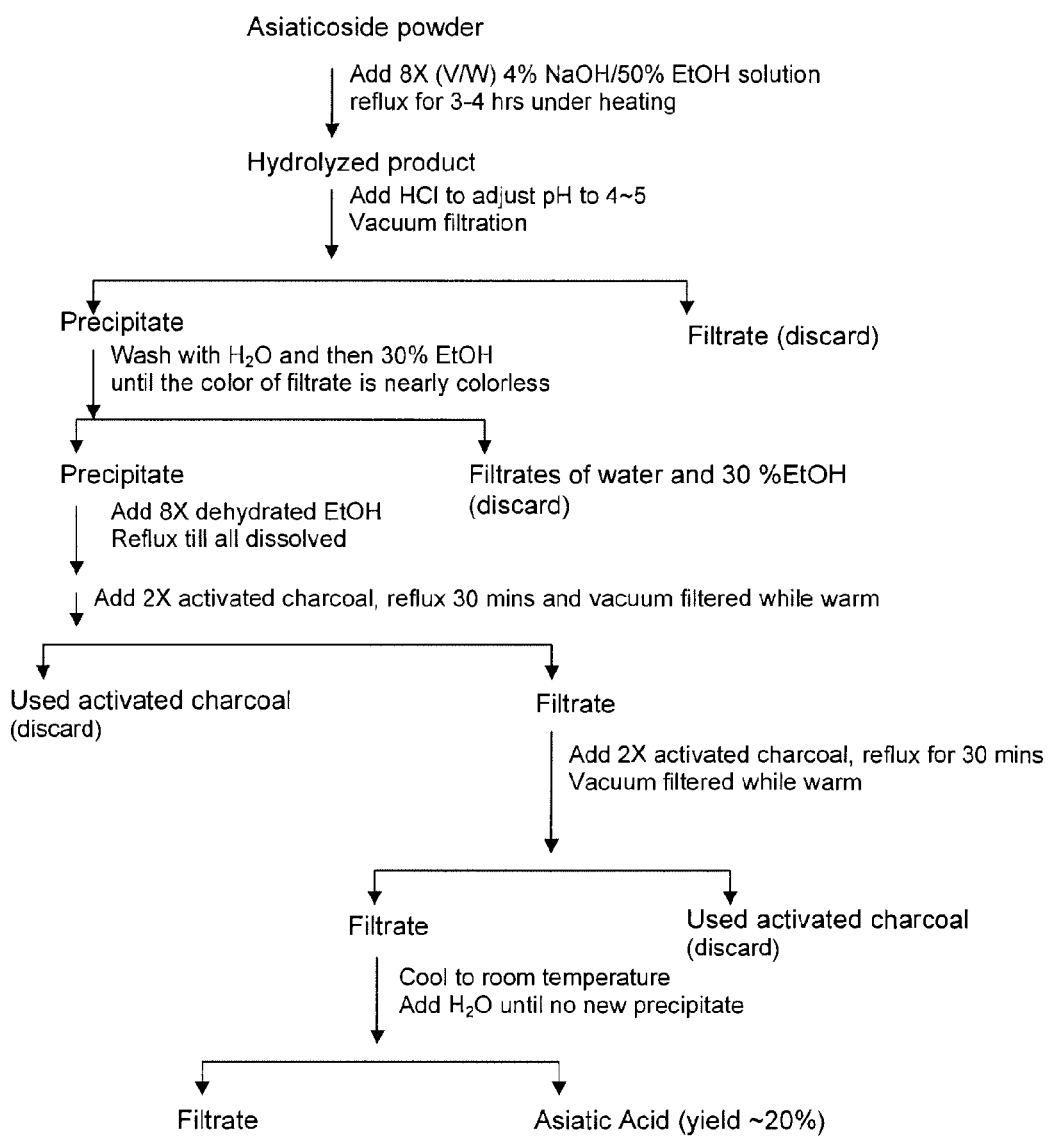

THERAPEUTIC FORMULATIONS BASED ON ASIATIC ACID AND SELECTED SALTS THEREOF

PRIORITY CLAIM

This application claims the benefit of priority of U.S. Provisional Application No. 61/006,432, filed on Jan. 11, 2008, which is incorporated herein by reference

BACKGROUND OF THE INVENTION

As first reported by Bontems, *Bull. Sci. Pharmacol.* 49: 186-91 (1941), asiatic acid and its trisaccharide asiaticoside can be extracted from *Centella asiatica*, a small, herbaceous annual, native to the Asian Pacific Rim, which is a member of the carrot and dill family, Apiaceae. The chemical structures of asiatic acid and asiaticoside are shown below:

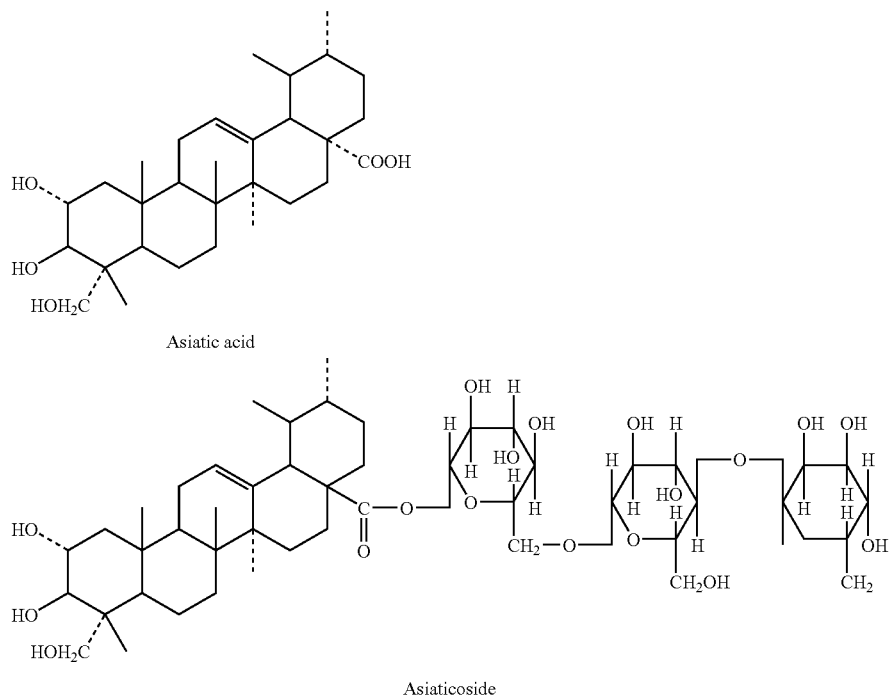

See Polonsky, *Compt. Rend.* 232: 1878-80 (1951), and *Bull. Soc. Chim.* 173-80 (1953).

The management of skin scars and chronic ulcers illustrates known uses for *C. asiatica* extracts that contain asiatic acid and asiaticoside. In a related vein, the literature also discloses employing *C. asiatica* extracts in the treatment of skin deformity associated with tuberculosis and leprosy. For example, see Boiteau et al., *Bull. Soc. Chim.* 31: 46-51 (1949).

For such wound healing, the pharmacological mode of action has been linked to the induction of keratinization, see May, *Eur. J. Pharmacol.* 4: 331-39 (1968), particularly through promoting skin fibroblast proliferation and synthesis of extracellular matrix components, including collagen I. For instance, see Lu et al., *Int'l Dermatol.* 43: 801-07 (2004); Skukla et al., *J. Ethnopharmacol.* 65: 1-11 (1999). According to Bonte et al., *Planta Med.* 60: 133-35 (1994), a comparison of asiaticoside and acid indicates that the former's sugar moieties seem unnecessary for this biological activity. As discussed in Grimaldi et al., *J. Ethnopharmacol.* 28: 235-41 (1990), moreover, asiaticoside is completely converted to plasma asiatic acid after oral administration to human subjects.

Knowledge of these wound-healing properties has informed proposals, in U.S. Pat. No. 5,834,437, of dermatological agents that include asiatic acid or one of its derivatives. See also U.S. Pat. No. 6,417,349, which speaks of a palliative effect, in a liver-fibrosis animal model, achieved by peritoneally administering a water-soluble extract of asiaticoside and madecassoside, a related compound also produced by *C. asiatica*. In addition to wound-healing and anti-fibrotic properties, orally administered asiaticoside has been reported to reduce the levels of spleen cells and inflammatory molecules, including COX-2, PGE2, TNF-alpha, and IL-6, with resultant inhibition or reduction of multiple arthritis parameters, such as paw swelling, arthritis score, and synovial hyperplasia in a standard (collagen-induced) rodent model of arthritis. See Li et al., *Yao Xue Xue Bao (Acta Pharma. Sinica)* 42: 698-703 (2007).

Although these and other disclosures implicate a therapeutic potential for asiatic acid and asiaticoside, realizing that potential has been hindered by the fact that extracting either compound has proved difficult, with relatively poor yields and low purity. In addition, little is known about producing salts of asiatic acid for use in therapeutic compositions. U.S. Pat. No. 6,891,063 describes certain asiatic acid salts, primarily with an ammonium cation, that are said to be suitable for topical treatment.

SUMMARY OF THE INVENTION

The present invention provides for high purity asiatic acid. In one embodiment, the asiatic acid is of pharmaceutical grade, preferably about 98% pure.

The present invention also provides for a salt produced from the high purity asiatic acid. The salt can be an alkali metal salt, or an alkaline earth metal salt, or an optionally substituted ammonium salt. Alternatively, the salt is a potassium salt. In another embodiment, the salt is a sodium salt. In yet another embodiment, the salt is a trometamol salt. The present invention provides for a solid dosage form that is comprised of any one or more of the aforementioned salts.

The present invention further provides for a derivative of the high purity asiatic acid. Illustrative of these derivatives are an amide or an ester. In a preferred embodiment, the derivative is asiaticoside.

In accordance with another aspect of the invention, a therapeutic composition is provided that is the product of a process comprising formulating high purity asiatic acid or asiaticoside with a pharmaceutically acceptable carrier to provide a dosage form that consists essentially of a therapeutically effective amount of asiatic acid or asiaticoside.

According to a further aspect, the present invention provides a methodology for treatment or prophylaxis of a fibrotic disease. The inventive methodology comprises administering to a subject suffering or at risk of suffering from such disease a therapeutic composition as described above. Exemplary of the fibrotic disease in this context is radiation-induced pneumonitis and fibrosis, idiopathic pulmonary fibrosis, diabetic nephropathy, and chronic obstructive pulmonary disease (COPD).

In yet another aspect of the invention, a method is provided for treatment or prophylaxis of an inflammatory disease, comprising administration to a subject suffering or at risk of suffering from such disease a therapeutic composition as described above. In this regard, the inflammatory-disease category is illustrated by arthritis, inflammatory bowel disease, and psoriasis.

BRIEF DESCRIPTION OF THE DRAWINGS

FIG. 1 shows HPLC trace overlays of asiatic acid starting material and salts produced.

FIG. 2 shows $^1$H-NMR spectroscopic analysis in DMSO-$d_6$ of asiatic acid Lot 071109 and sodium salt AJF09,99b, at 300 MHz.

FIG. 3 shows $^{13}$C-NMR spectroscopic analysis in DMSO-$d_6$ of asiatic acid Lot 071109 and sodium salt AJF09,99b, at 300 MHz.

FIG. 4 shows $^{13}$C-NMR spectroscopic analysis in DMSO-$d_6$ of asiatic acid Lot 071109 and sodium salt AJF09,99b, from 300 MHz at 11 ppm to 41 ppm.

FIG. 4a shows complete $^1$H-NMR spectrum of asiatic acid in DMSO-$d_6$.

FIG. 4b shows magnified view of asiatic acid 1H-NMR spectrum.

FIG. 4c shows complete $^1$H-NMR spectrum of asiatic acid sodium salt (AJF09,99b).

FIG. 4d shows magnified view of asiatic acid $^1$H-NMR spectrum.

FIG. 4e shows $^{13}$C-NMR spectrum of asiatic acid in DMSO-$d_6$.

FIG. 4f shows magnified view of an asiatic acid $^{13}$C-NMR spectrum.

FIG. 4g shows the complete $^{13}$C-NMR spectrum of asiatic acid sodium salt in DMSO-$d_6$.

FIG. 4h shows magnified view of asiatic acid sodium salt $^{13}$C-NMR spectrum.

FIG. 5a shows PXRD of asiatic acid.

FIG. 5b shows PXRD of a sodium salt of asiatic acid.

FIG. 6 shows the FTIR spectrum of asiatic acid.

FIG. 7 shows the FTIR spectrum of an asiatic acid sodium salt (AJF09,82).

FIG. 8 shows the FTIR spectrum of an asiatic acid sodium salt (AJF09,99b).

FIG. 9 shows the FTIR spectrum of an asiatic acid sodium salt (AJF09,99a).

FIG. 10 shows TGA Thermogram of asiatic acid.

FIG. 11 shows TGA Thermogram of asiatic acid sodium salt AJF09,82.

FIG. 12 shows TGA Thermogram of asiatic acid sodium salt AJF09,99b.

FIG. 13 depicts a standard linearity curve.

FIG. 14 provides a schematic representation of a process for asiaticoside production.

FIG. 15 provides a schematic representation of a process for producing pharmaceutical-grade asiatic acid.

DETAILED DESCRIPTION OF THE PREFERRED EMBODIMENTS

Figure 16A:
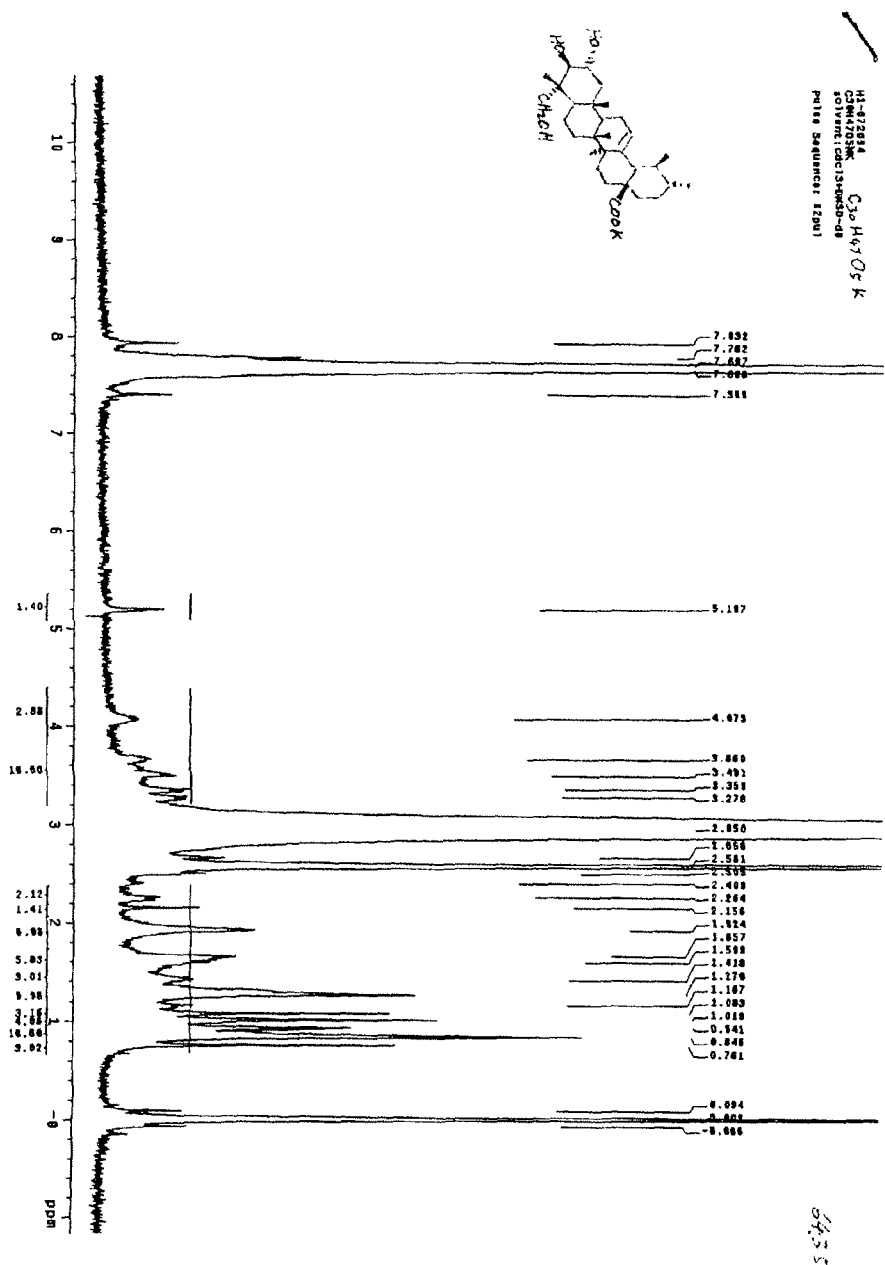
FIG. 16a shows the $^1$H-NMR of an asiatic acid potassium salt.

In light of the problems detailed above, the present inventors have developed a readily implemented protocol for obtaining both asiaticoside and asiatic acid in a high purity, suitable for pharmacological development. Furthermore, they have produced and characterized salts of asiatic acid that possess the requisite physical properties for therapeutic formulation, particularly for treating conditions associated with inflammation and fibrosis.

I. Production of Pharmaceutical-Grade Asiatic Acid

A. Preparing 92% Pure Asiaticoside

Crude asiaticoside powder is commercially available, for example, from Guangxi Changzhou Natural Product Co. Ltd. (www.changzhou-centella.com).

To crude asiaticoside powder was added 4×60% EtOH (V/W). The mixture was refluxed with heating at a temperature range of about 70° C. to about 90° C. (e.g., 80° C.) until the solid was dissolved. The solution was cooled down and placed in a 5° C. cold room for crystallization for 16 hours. An amorphous precipitate formed and was filtered out. The recovered precipitate was washed with 60% EtOH until its color turned white. Then the precipitate was oven dried at a temperature range of about 55° C. to about 70° C. (e.g. 60° C.) and at a reduced pressure in the range of about −0.09 to −0.11 MPa, for example, −0.10 MPa.

To the dried precipitate was added 30× (V/W) 80% acetone aqueous solution. The mixture was refluxed with heating for 1 hour before the solid was dissolved. The solution was filtered and the filtrate was placed in a 10° C. cold room for crystallization for 24 hours. An amorphous precipitate formed and was filtered out. The recovered precipitate was washed with 80% acetone until its color turned white. The precipitate was dried and the dried solid was ground to yield asiaticoside powder. FIG. 14 shows a summary of the process.

B. Preparing 98% Pure Asiatic Acid 200 grams of asiaticoside powder prepared as described above (purity approximately 92%) were dissolved in 8× (V/W) 4% NaOH/50% EtOH solution (1600 ml). The resultant solution was refluxed for about 3-4 hours in an 80° C. water bath, and then cooled down to room temperature or close to room temperature.

The pH of this solution then was adjusted to between 4 and 5 by adding diluted HCl (pre-diluted 1~2 fold) gradually by small portions (e.g., approximately 10 ml each time) with continuous stirring. A precipitate continually came out in the process and finally formed a sticky batter.

This batter was placed into a 200 mm Buchner funnel for vacuum filtration at reduced pressure. The filtrate was discarded. The precipitate was washed with water under vacuum until the color of the filtrate coming out was nearly colorless. Then the precipitate was washed with 30% EtOH until the color of the filtrate coming out was nearly colorless. The filtrates of these two washes were discarded.

8× (V/W) of anhydrous EtOH (about 1600 ml) was added to the precipitate and then the mixture was refluxed with heating in an 80° C. water bath until the precipitate was entirely dissolved. 2× (about 400 g) activated charcoal was then added and the solution was continuously refluxed for an additional 30 minutes. The charcoal was filtered out while the solution was still warm with a 200 mm Buchner funnel with vacuum filtration at a reduced pressure. The used activated charcoal was discarded. Another batch of activated charcoal of the same weight was then added to the filtrate. The mixture was subjected to reflux for another 30 minutes and vacuum filtered while it was still warm with a 200 mm Buchner funnel at a reduced pressure.

The filtrate was cooled down to room temperature. To the filtrate water was added in batches, each about 100-200 ml, until there was no additional white precipitate coming out. The total volume of water needed was approximate 4000 ml. The solution was then vacuum filtered with a 200 mm Buchner funnel at a reduced pressure. The filtrate was discarded. The white solid in the funnel was then dried, and the dried solid was ground to yield an asiatic acid material of 98% (W/W) purity. FIG. 15 shows a summary of the process.

II. Pharmacological Activity of Asiatic Acid

Bleomycin treatment of rats is the preferred approach to establishing an animal model for fibrosis. As described in greater detail below, the asiatic acid and asiaticoside compositions of the present invention significantly enhance survival of rats treated with bleomycin, regardless of whether treatment is initiated one day or seven days after bleomycin administration. This is an unexpected result in light of the fact that dexamethasone, conventionally used to treat pulmonary fibrosis, does not significantly enhance rat survival in this context.

Because the primary effects of dexamethasone are on inflammation pathways, the results obtained with the present invention indicate that, in addition to inhibitory effects on inflammatory processes, asiatic acid and asiaticoside also exert effects on other pathways that are related to or are directly involved in fibrosis. For instance, as determined by lung histopathology, asiatic acid reduces the extent of bleomycin-induced lung fibrosis. It is more effective than dexamethasone when treatment with asiatic acid or dexamethasone is initiated seven days after bleomycin insult, indicating that asiatic acid not only targets the inflammatory process but also has a more direct effect than dexamethasone on fibrosis.

Much better than dexamethasone, asiatic acid and asiaticoside significantly decrease bleomycin-induced lung fibrosis, as measured by lung weight to body weight ratio, regardless of whether treatment is initiated one day or seven days after bleomycin insult.

Asiatic acid and asiaticoside also significantly decrease bleomycin-induced fibrosis, as measured by serum levels of hydroxyproline (collagen precursor) and type III collagen. The impact of asiatic acid in this context is as good or slightly better than dexamethasone, regardless of whether treatment is initiated one day or seven days after bleomycin exposure.

Asiatic acid significantly reduces bleomycin-induced serum levels of fibrosis-mediating cytokines transforming growth factor beta (TGF-β) and tumor necrosis factor alpha (TNF-α), which is comparable to dexamethasone, regardless of whether treatment is initiated one day or seven days after exposure to bleomycin.

III. Therapeutic Indications and Formulations

The results detailed in this description thus underscore the usefulness of pharmaceutical-grade asiatic acid and high-purity asiaticoside, produced in accordance to the present invention, for treating a range of diseases associated with inflammation, as well as those associated with fibroblast and matrix accumulation ("fibrotic diseases"). Illustrative of the class of inflammatory diseases are psoriasis, inflammatory bowel disease, including Crohn's disease and ulcerative colitis, and arthritis, including rheumatoid arthritis, osteoarthritis and psoriatic arthritis. The progression of these diseases is marked by aberrant immune system activation and elevated levels of inflammatory molecules, such as COX-2, and certain cytokines and prostaglandins. Illustrative of the class of fibrotic diseases are radiation-induced pneumonitis and fibrosis, idiopathic pulmonary fibrosis, and diabetic nephropathy, the progression of which is marked by renal fibrosis.

It is an aspect of the invention, therefore, to provide therapeutic compositions prepared by formulating high-purity asiatic acid or asiaticoside with other components conventionally employed to produce a medicament, especially for internal use. Thus, a therapeutic composition of the invention may include one or more pharmaceutically acceptable carriers, excipients, or stabilizers as described, for example, in REMINGTON—THE SCIENCE AND PRACTICE OF PHARMACY $21^{st}$ ed. (2005), so long as the anti-fibrotic effect of the high-purity asiatic acid or asiaticoside is not adversely affected by the other component(s) of the composition.

Partly as a function of the desired mode of administration, a therapeutic composition of the invention could be formulated for injection, as for parenteral delivery. To this end, the therapeutic composition could be produced as an aqueous solution, comprised of a physiologically compatible buffer such as Hank's solution, Ringer's solution, or physiological saline buffer.

Pursuant to another embodiment of the invention, a salt of asiatic acid (see next section) would be compounded with a pharmaceutically acceptable solid matrix, to provide a solid dosage form that is suitable for oral, buccal, sublingual, rectal, or vaginal administration, inter alia. In accordance with this aspect of the invention, the therapeutic composition would be the product of combining high-purity asiatic acid or asiaticoside, or a salt of asiatic acid, with one or more solid excipients, optionally grinding the resulting mixture, and then processing the mixture, possibly after the addition of suitable auxiliaries, to obtain tablets or dragee cores. Suitable excipients in this regard are fillers, such as sugars (lactose, sucrose, mannitol, sorbitol, etc.) and cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). A disintegrating agent also may be added, such as cross-linked polyvinylpyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Among the therapeutic compositions of the invention that are suitable for oral administration are push-fit capsules made of gelatin, as well as soft, sealed capsules made of gelatin, and a plasticizer, such as glycerol or sorbitol, to contain a solid formulation produced with high-purity asiatic acid or asiaticoside. In keeping with the description above, a push-fit capsule in this regard could contain the active component in admixture with filler such as lactose, binders such as starches, and/or lubricants such as talc or magnesium stearate, optionally with one or more stabilizers. In soft capsules, the active component could be in solution or suspended in a suitable liquid, such as a fatty oil, liquid paraffin, or liquid polyethylene glycol (PEG), again with stabilizer(s) optionally added.

Another manner for administering a therapeutic composition of this invention is by inhalation or insufflation, which delivers a therapeutic agent directly to the respiratory tract. See, for example, U.S. Pat. No. 5,607,915 and published PCT applications WO 97/39745 and WO 99/47196. To this end, the invention contemplates a liquid formulation that is suitable for administration via a nebulizer, a liquid spray device, or an electrohydrodynamic (EHD) aerosol device.

In one embodiment, such a composition would include a pharmaceutically acceptable carrier that is a liquid, such as an alcohol, water, polyethylene glycol or a perfluorocarbon. Optionally, another material can be added to alter the aerosol properties of the solution or suspension of the active ingredient, as described herein. This other material could be a liquid, such as an alcohol, glycol, polyglycol or a fatty acid. Other approaches are available for formulating a liquid solution or suspension, in accordance with the invention, that is suitable for use in aerosol devices. See U.S. Pat. No. 5,112,598 and No. 5,556,611.

For administering an air-borne composition of the invention, another format employs a dry powder carrier, suitable for a dry-powder inhaler. Illustrative of such carriers are: the monosaccharides, such as fructose, mannitol, arabinose, xylitol and dextrose (glucose) and their nionohydrates; disaccharides such as lactose maltose or sucrose; and polysaccharides, e.g., starches, dextrins, and dextrans. For instance, an asiatic acid salt of the invention could be formulated into a dry powder with one or more of these carrier materials, using a micronizer as described generally in U.S. Pat. No. 5,376,386.

IV. Production and Characterization of Asiatic Acid Salts for Pharmacological Use In view of good solubility of asiatic acid in methanol, the present invention contemplates the formation of salts of asiatic acid, e.g., by dissolving the acid in methanolic sodium hydroxide, methanolic sodium carbonate and methanolic ammonium hydroxide solutions, respectively. The production and characterization of asiatic acid salts are described in greater detail below.

A. Salt Screening for Asiatic Acid

Owing to the good solubility of asiatic acid in methanol (see below), salts of asiatic acid can be formed by dissolving it in methanolic sodium hydroxide, methanolic sodium carbonate and methanolic ammonium hydroxide solutions, respectively.

1. Asiatic Acid—Sodium Carbonate (AJF09, 82)

Asiatic acid (0.992 g) was dissolved in 27.5 mL of methanol. Anhydrous sodium carbonate (2.0043 g) was added to the methanol solution and shaken vigorously. The methanol-asiatic acid solution was transferred to a round bottom flask and evaporated to dryness. A fine white powder of asiatic acid sodium salt was produced and dried in a vacuum oven at 100° C. for 2 hours; approximately 1 g of sample was recovered.

2. Asiatic Acid in Methanolic Ammonium Hydroxide (AJF09,99a)

About 6 mL of methanolic ammonium hydroxide were added dropwise to 0.4923 g of asiatic acid. Most of the sample had gone into solution and new flaky material began appearing. An additional 1 ml of methanolic ammonium hydroxide was added, and the solution was left stirring overnight. A precipitate formed and was collected by filtration, and 0.0741 g of asiatic acid ammonium salt was recovered.

3. Asiatic Acid in Methanolic Sodium Hydroxide (AJF09, 99b)

Asiatic acid (0.4961 g) was dissolved in 7.0 mL of 0.2 M methanolic sodium hydroxide. Once fully dissolved saturated sodium chloride solution was added drop wise until solution turned cloudy and precipitation occurred. Deionized water (7.0 mL) was added to dissolve any NaCl present. Precipitate was collected by filtration and dried in a vacuum oven at 100° C. for 2 hours; 0.4938 g of asiatic acid sodium salt was recovered.

4. Asiatic Acid Potassium Salt

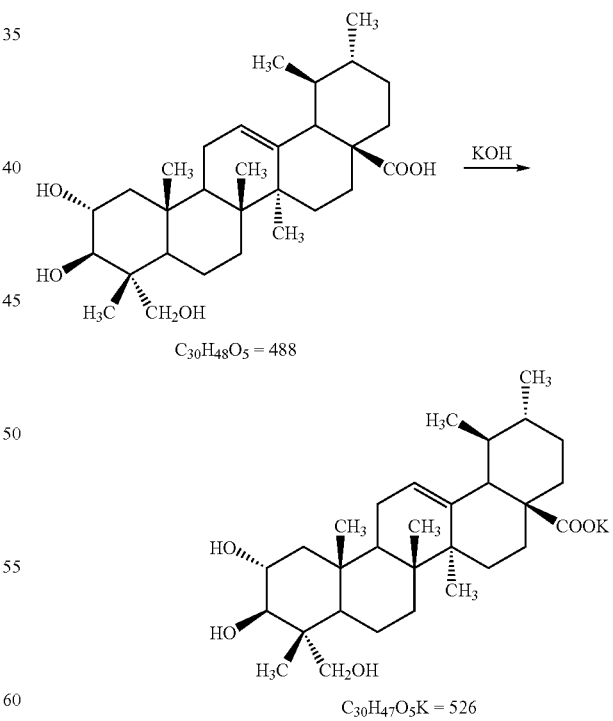

Figure 17A:
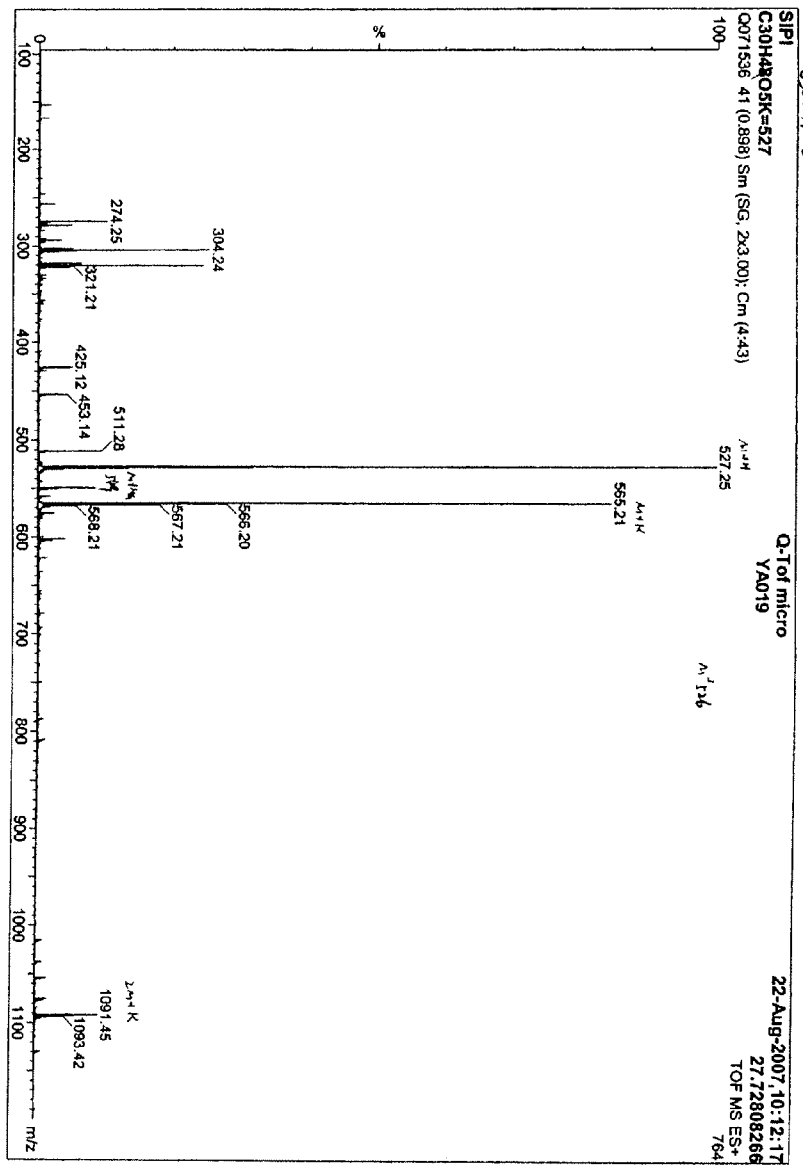
FIG. 17a shows the mass spectroscopy of an asiatic acid potassium salt.

With reference to scheme 4 above, asiatic acid 4 g (8.196 mmol) were added to methanol (30 ml). The mixture was heated to dissolve. To the solution was added a solution made of KOH 0.56 g (8.187 mmol) and methanol 20 ml until the pH became 8-9. The resultant solution then was decolorized, with activated charcoal, and concentrated. To the concentrated solution was added a sufficient quantity of acetone to homogenize, and the solution was cooled down. A precipitate formed and was filtered out to yield 3.5 g of asiatic acid potassium salt as off-white crystals. FIG. 16a shows the $^1$H-NMR of the product. FIG. 17a shows the mass spectroscopy of the product.

5. Asiatic Acid Trometamol Salt

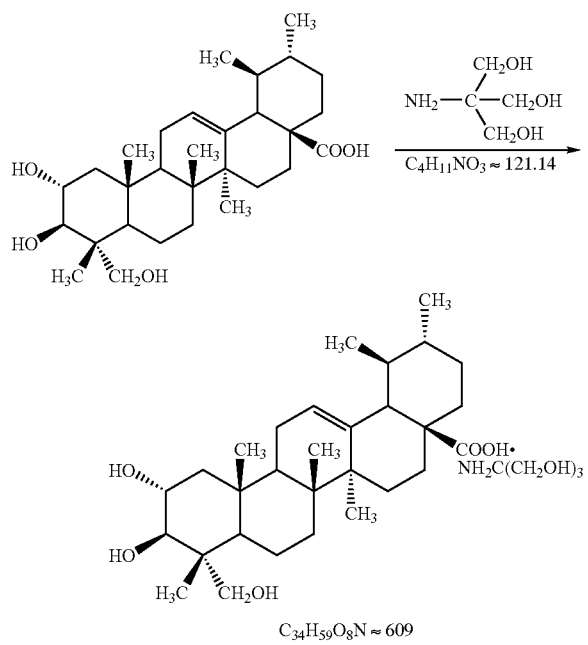

Figure 16B:
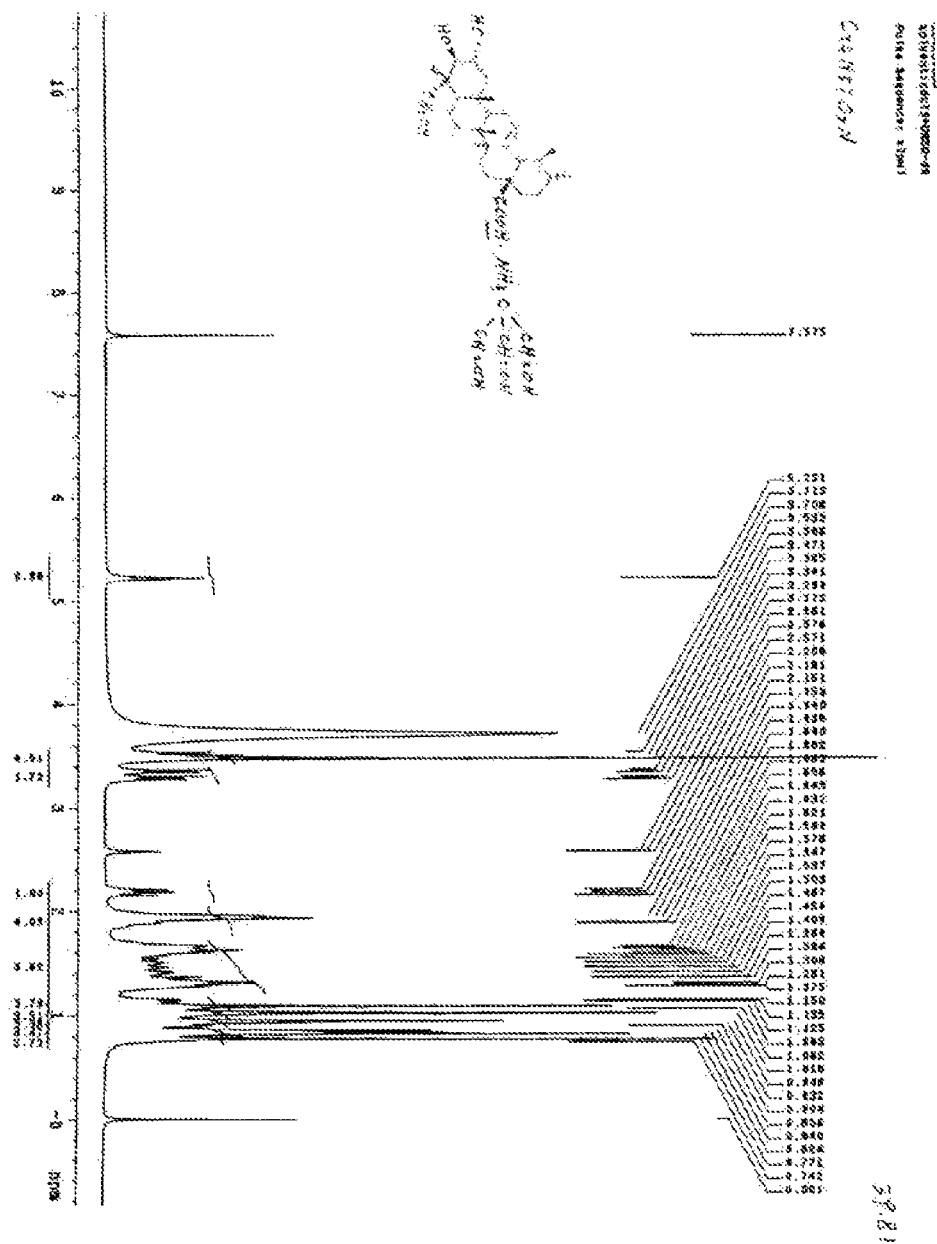
FIG. 16b shows the $^1$H-NMR of an asiatic acid trometamol salt.
Figure 17B:
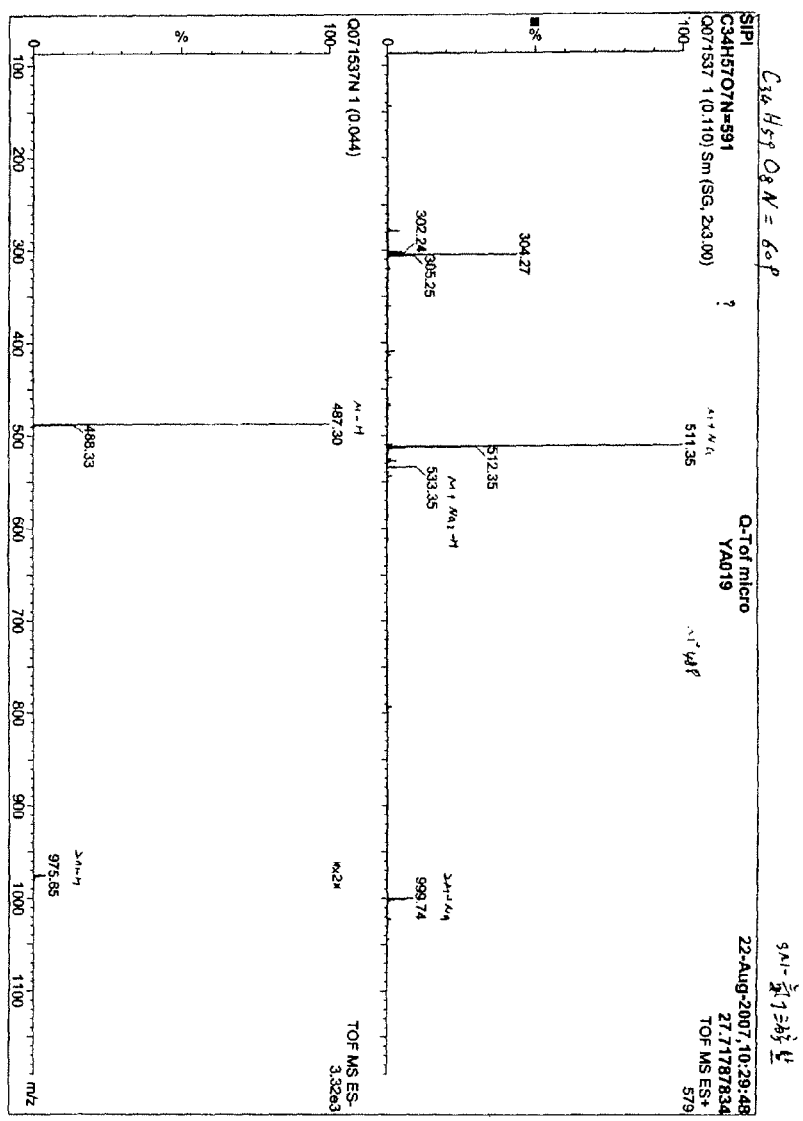
FIG. 17b shows the mass spectroscopy of an asiatic acid trometamol salt.

With reference to scheme 5 above, asiatic acid 2 g (4.09 mmol) and trihydroxymethylaminomethane (tromethamine) 0.59 g (4.623 mmol) were added to methanol (30 ml). The mixture was stirred at room temperature for 24 hours and was refluxed for 0.5 hour. The solution was concentrated, to which was added a small quantity of water. A precipitated formed and was then filtered out. The filter cake was placed in methanol to dissolve with heat. The resultant solution was filtered to get rid of the insoluble substances, and then concentrated. To the concentrated solution was added a sufficient quantity of acetone to homogenize. The solution was cooled down. A precipitate formed, was filtered out, and was dried under 50° C. to yield 1.5 g of asiatic acid trometamol salt as an ecru solid. FIG. 16b shows the $^1$H-NMR of the product. FIG. 17b shows the mass spectroscopy of the product.

6. Asiatic Acid Sodium Salt-Sodium Phosphonate

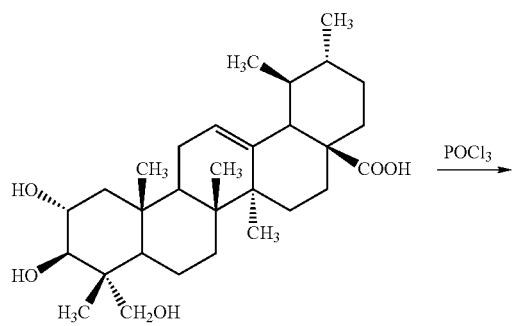

With reference to the first step in scheme 6 above, pyridine (12 ml) was cooled down with icy salt water to −10° C., to which was added phosphonium hydroxide 2.2 g (0.01435 mol) in drops. Two minutes later, a solution of asiatic acid 2 g (0.004098 mol) and pyridine (6 ml) in drops was added. The mixture was stirred to react for 1.5 hours. To the reaction mixture were slowly added 40 ml of ice water. The mixture was stirred at room temperature overnight. Most solvent was evaporated to afford a solid which was dried under reduced pressure. The solid was added into 4N HCl (20 ml), a jelly material precipitated, and was filtered out. The filter cake was washed with water to yield a crude product. The crude product was dissolved in methanol. The solution was decolorized with activated charcoal, and concentrated. To the concentrated solution was added a sufficient quantity of acetone to homogenize. A precipitate formed and was filtered out to yield a jelly-like phosphate ester.

Figure 16C:
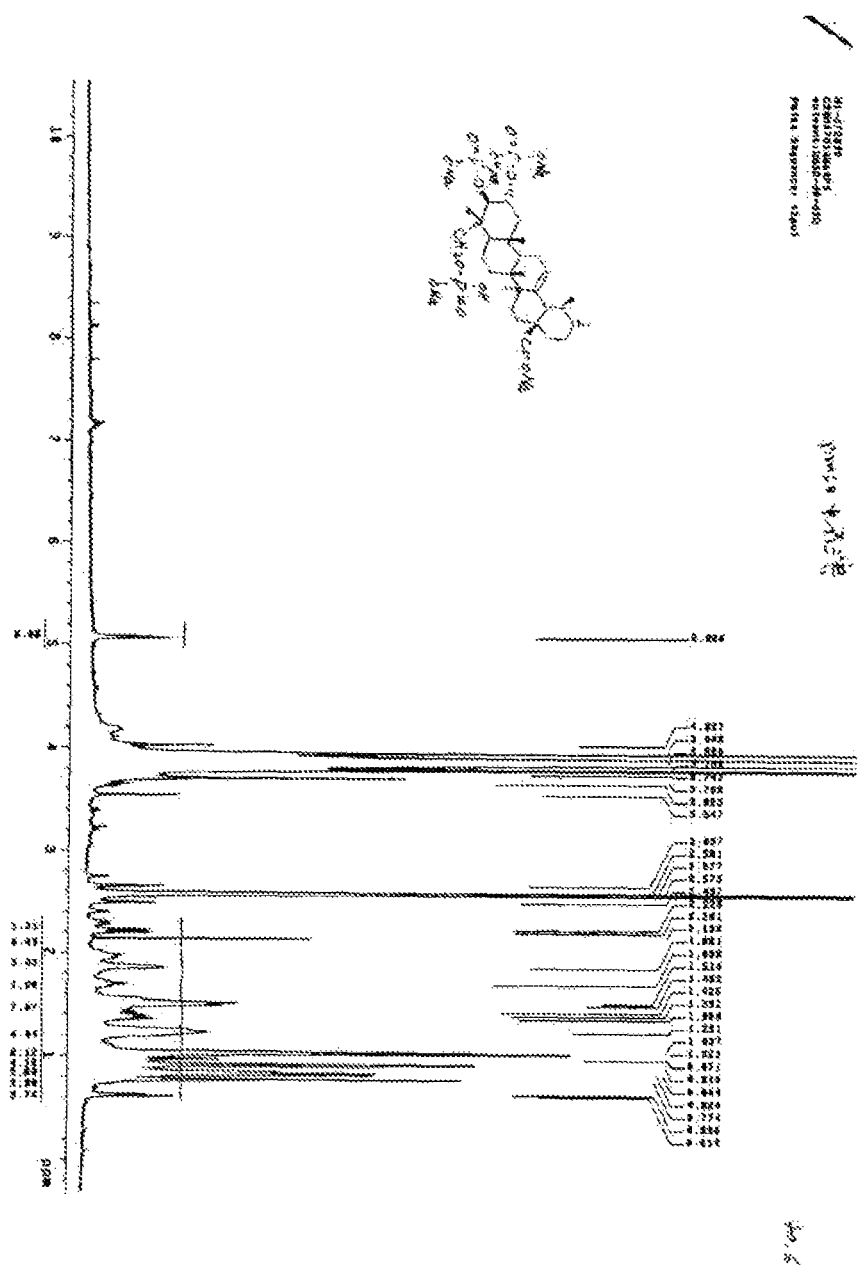
FIG. 16c shows the $^1$H-NMR of an asiatic acid sodium salt-sodium phosphonate.
Figure 17C:
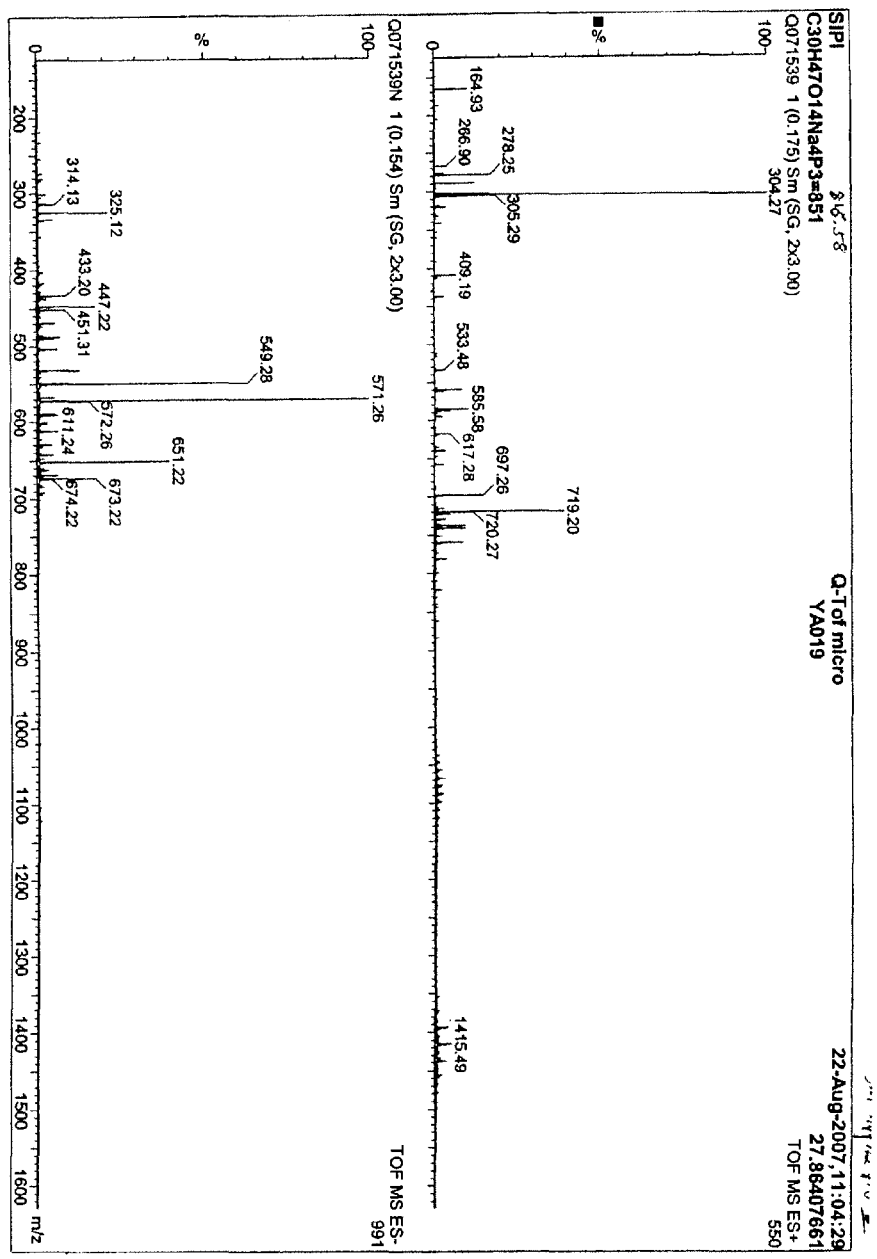
FIG. 17c shows the mass spectroscopy of an asiatic acid sodium salt-sodium phosphonate.

With reference to the last step in scheme 6, the above crude product was dissolved in methanol. To the solution was added 1N sodium hydroxide methanol solution until the pH became 8-9. The solution was decolorized with activated charcoal, and concentrated. To the concentrated solution was added a sufficient quantity of acetone to homogenize. The solution was cooled down. A precipitate formed and was filtered, dried under 50° C. to afford 2.2 g of asiatic acid sodium salt-sodium phosphonate as an ecru solid. FIG. 16c shows the ¹H-NMR of the product. FIG. 17c shows the mass spectroscopy of the product.

7. Asiatic Acid Triacetate-Amide Derivative

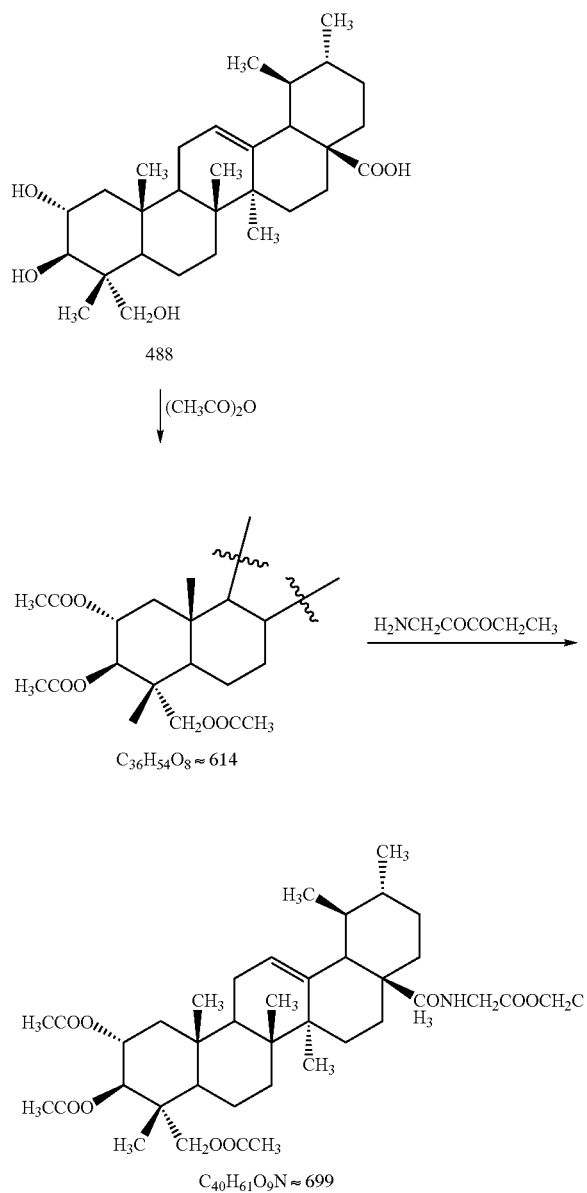

With reference to the first step in scheme 7 above, asiatic acid (5 g) was dissolved in pyridine (10 ml) with stirring. The solution was cooled down to 10° C., and 15 ml of acetic anhydride were added. The resultant solution was stirred at room temperature for 20 hours, and then 200 ml of ice water were added. A precipitate formed, was filtered out and washed with water, and then was dried under 50° C. to yield 6.28 g of asiatic acid triacetate as a white powder.

With reference to the second step in scheme 7, asiatic acid triacetate 6.5 g (0.01058 mol) was added to 100 ml dichloromethane. The solution was cooled with ice water, and then triethylamine 1.2 g (0.01186 mol), ethylglycinate hydrochloride 1.55 g (0.0111 mol) and 4-dimethylamino pyridine 0.2 g (0.00164 mol) were added. The mixture was stirred at 0-5° C. for 0.5 hour. To the mixture was added a solution of DCC 2.37 g (0.0115 mol) and dichloromethane (50 ml) in drops over 0.5 hour. The reaction was stirred at 0-5° C. for 2 hours and then kept at room temperature for 24 hours. The solid was filtered out. The filtrate was washed with 1N HCl, with saturated NaHCO$_3$ solution, and then with water to neutral pH. The solvent was evaporated under reduced pressure, yielding 9 g of asiatic acid triacetate-amide derivative as a gel-like material.

Figure 16D:
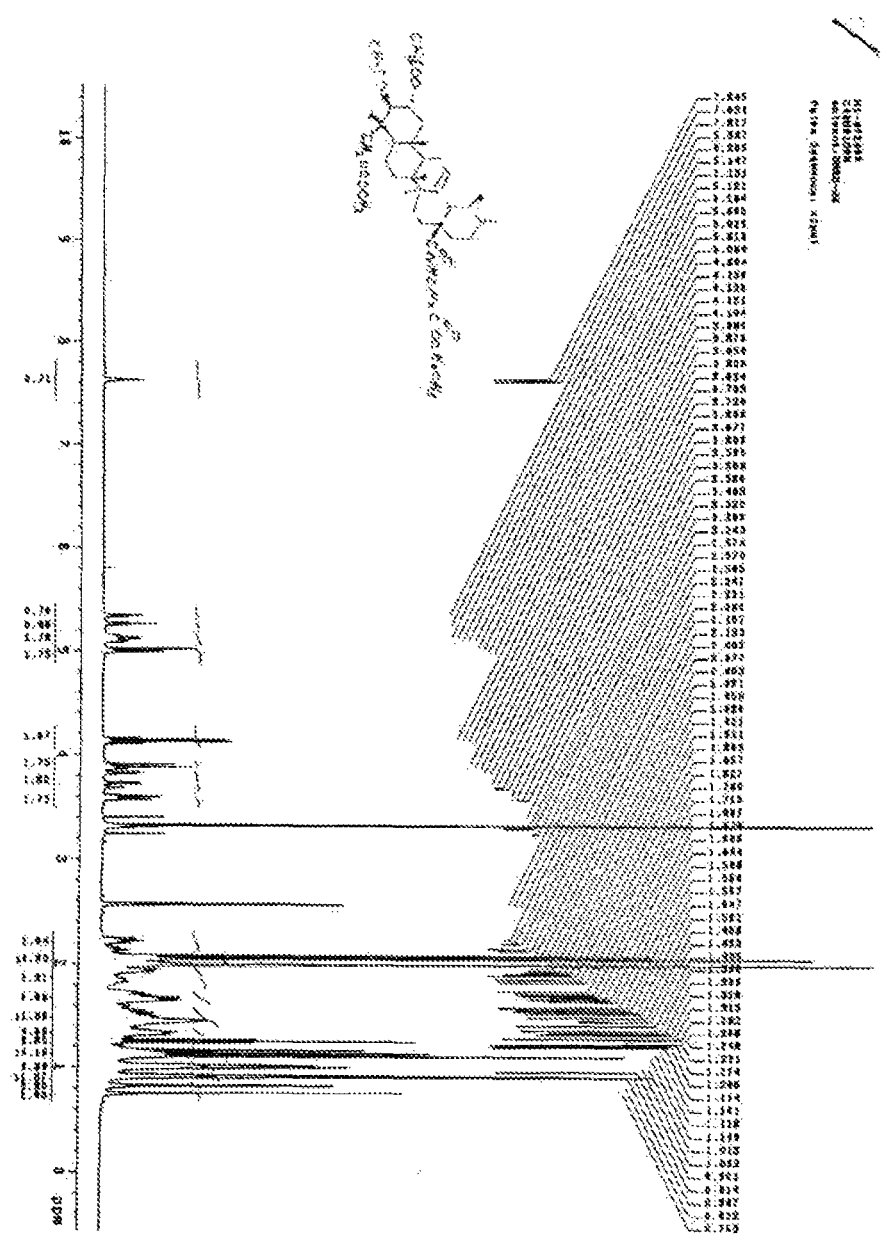
FIG. 16d shows the $^1$H-NMR of an asiatic acid triacetate-amide derivative.
Figure 17D:
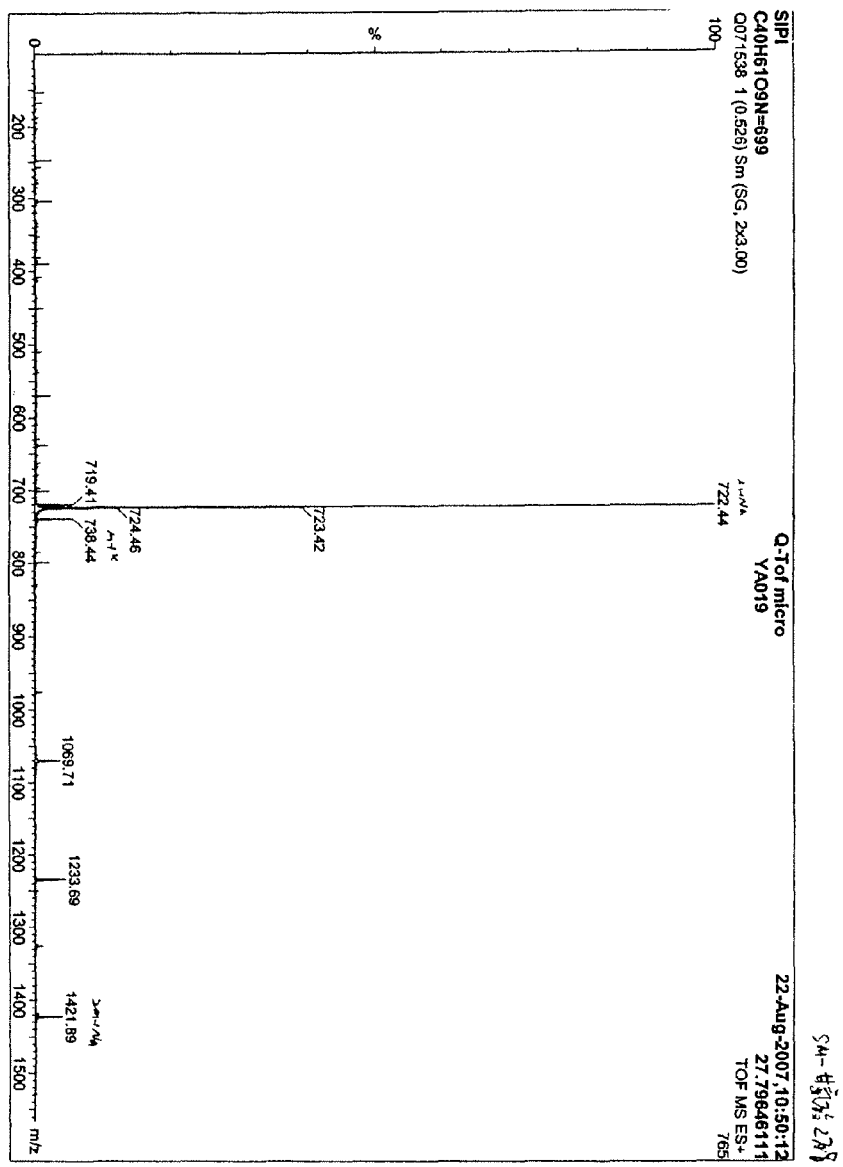
FIG. 17d shows the mass spectroscopy of the asiatic acid triacetate-amide derivative.

The crude, gel-like product was placed on a silica gel column, and eluted with dichloromethane+acetone (20:1). The product fraction was collected and concentrated. Solid was filtered out and the filtrate was vacuum dried to yield 2.82 g white crystal. FIG. 16d shows the ¹H-NMR of the product. FIG. 17d shows the mass spectroscopy of the product.

B. HPLC Analysis of Asiatic Acid Salts

Certain asiatic acid salts, produced as described above, were subjected to HPLC analysis.

Standard Preparation

Approximately 5 mg of asiatic acid were transferred into a 25 mL volumetric flask, and 1 mL of methanol was added and mixed well, until the acid had dissolved in the methanol. The volumetric flask then was brought to volume with mobile phase and mixed well.

Chromatographic Parameters

| Column: | Agilent, Zorbax Eclipse XDBC8, 250 mm × 4.6 mm |
|---|---|
| Mobile phase: | KH$_2$PO$_4$ (3 g/L) pH 2.5/Acetonitrile (55:45) |
| Flow rate: | 1.0 mL/min |
| Wavelength: | 204 nm |
| Injection volume: | 10 µL |
| Column Temperature: | 30° C. |
| Run Time: | 20 minutes |

System Suitability

System reproducibility was demonstrated for each chromatographic run performed with six (6) replicate injections of the Working Standard solution (200 µg/mL of asiatic acid in methanol). The percentage relative standard deviation (% RSD) for replicate injections was calculated. Tailing factor and number of theoretical plates for asiatic acid was calculated in the first injection of Working Standard solution, used for RSD.

Acceptance Criteria

% RSD of the peak area response for Peak 1 from the six (6) replicate injections may not be greater than 3.0%.

Number of theoretical plates should be NLT 10000.

Tailing factor should be NMT 1.5.

Resolution NLT 2.0.

Results

| | Asiatic Acid |
|---|---|
| % RSD | 0.5 |
| # of Theoretical Plates | 15322 |
| Tailing Factor | 1.0 |
| Resolution | 2.7 |

Recovery for each salt and starting material was calculated (Table 1). Retention time of asiatic acid salts were the same as the asiatic acid starting material, thus confirming that the salts had not undergone any significant structural changes (FIG. 1).

TABLE 1

Recovery for Asiatic Acid and Salts

|  | Area Response (µV *sec) | Average Area Response (µV *sec) | % Recovery (µV *sec) |
| --- | --- | --- | --- |
| Asiatic acid Std | 1005566 | 1005566 | 100.00 |
| Sodium Salt (From Carbonate) | 905119 902523 | 903820.5 | 92.69 |
| Sodium Salt from Methanolic NaOH | 945697 950890 | 948293.5 | 96.52 |
| Ammonium Salt | 1077786 1082316 | 1080050.75 | 101.12 |

Solubility in Water and Methanol

Solubility results were obtained for asiatic acid and one of the sodium salts (AJF09,99b) in water and methanol. Table 2 enumerates the results. Asiatic acid was only sparingly soluble in water (0.03 mg/ml), whereas the sodium salt was some 228-times more soluble. This is strong evidence for salt formation and highlights a very significant increase in pharmaceutical utility, with respect to dosage form preparation.

Sample Preparation

Saturated solutions obtained from starting material and salt in methanol and water were filtered and diluted accordingly with mobile phase. No dilution was performed for asiatic acid in water. Samples were prepared in triplicate except for the sodium salt prepared in methanol, for which two preparations were done.

TABLE 2

Solubility Results

| Sample Name | Area (µV *s) | Solubility [mg/mL] |
| --- | --- | --- |
| Asiatic acid raw material inj 1A (water) | 121575.00 | 0.03 |
| Asiatic acid raw material inj 1B (water) | 181180.00 | 0.04 |
| Asiatic acid raw material inj 1C (water) | 84600.00 | 0.02 |
| Asiatic acid raw material inj 1A (MeOH) | 600450.00 | 34.87 |
| Asiatic acid raw material inj 1B (MeOH) | 468690.00 | 27.22 |
| Asiatic acid raw material inj 1C (MeOH) | 640580.00 | 37.20 |
| Asiatic acid-Na salt NaOH inj 1A ($H_2O$) dil. | 210980.00 | 6.86 |
| Asiatic acid-Na salt NaOH inj 1B ($H_2O$) dil. | 195600.00 | 6.36 |
| Asiatic acid-Na salt NaOH inj 1C ($H_2O$) dil. | 224970.00 | 7.32 |
| Asiatic acid-Na salt NaOH inj 1A (MeOH) | 438105.00 | 25.44 |
| Asiatic acid-Na salt NaOH inj 1B (MeOH) | 414550.00 | 24.08 |

C. Nuclear Magnetic Resonance (NMR) Spectroscopy

Preliminarily, $^1$H-NMR and $^{13}$C-NMR spectroscopic analysis in DMSO-$d_6$ was carried out on a Varian 300 MHz instrument on both asiatic acid starting material and sodium salt AJF09,99b. Generally, the obtained proton NMR spectrum evidences the chemical shifts and splitting patterns (multiplicity) consistent with the structure of asiatic acid (FIG. 2). By comparing the spectra of both compounds it is evident that some signals have changed chemical shifts, especially between 4.0 and 4.6 ppm. This is indicative of electronic changes consistent with salt formation.

$^{13}$C-NMR data show the chemical shifts of carbons consistent with the structure of asiatic acid. FIGS. 3 and 4 depict the representative $^{13}$C spectra of both asiatic acid starting material and a sodium salt thereof. Carbon signals with chemical shifts around 36, 24 and 17 ppm in the spectra of asiatic acid have changed in the spectra of the sodium salt, also indicating salt formation.

Additional NMR analysis was performed at 400 MHz, in order to obtain a more resolved profile and to confirm the preliminary results. A detailed analysis of both proton and carbon NMRs (see FIGS. 4a-h) reveals that the molecular structure of the sodium salt essentially remains the same, except for observed chemical shift differences generated by the effect of the new sodium carboxylate. Among the most relevant differences supporting the incidence of salt formation are:

a. Asiatic acid exhibits a proton at 11.9 ppm usually correlated to a carboxylic acid functional group. This signal is not present in the sodium salt.

b. The chemical shift of the unique carboxylic carbon is different in both analyzed materials; again, the conversion from carboxylic to carboxylate would explain this behavior.

D. Powder X-Ray Diffraction

X-Ray diffraction was performed using a Shimadzu Lab X, XRD-6000 in compliance with USP <941>. FIG. 5a shows the diffractogram for asiatic acid. The broad band observed is characteristic of amorphous materials. When the protocol set out above in section IV.A.3 was scaled up to produce the sodium salt at the 2-gram scale, results from HPLC analysis tracked those detailed in section IV.B, supra, and powder x-ray diffraction data were consistent with a crystalline character for the obtained material (see FIG. 5b).

E. Fourier Transform Infrared Spectroscopy (FTIR)

FTIR spectroscopic analysis was performed on asiatic acid, on the sodium salts AJF09,82 and AJF09,99b, and on the ammonium salt (AJF09,99a). FIG. 6 is exemplary of the resulting infrared spectrum of Asiatic acid and is typical of a carboxylic acid, as evidenced by the presence of the acid carbonyl band near 1697 $cm^{-1}$.

The infrared spectra obtained for sodium salts AJF09,82 (FIG. 7) and AJF09,99b (FIG. 8) clearly evidence the decreased intensity of the carbonyl band near 1697 $cm^{-1}$ and the appearance of bands near 1545 and 1390 $cm^{-1}$. Presence of the later bands is attributable to the presence of a carboxylate group, as opposed to a carboxylic acid group. This is spectroscopic evidence of salt formation. The infrared spectrum of the ammonium salt AJF09,99a (FIG. 9) shows the presence of a band around 1390 $cm^{-1}$, likewise indicative of a salt. The characteristic band for carboxylic acids around 1690 $cm^{-1}$ still is present, which may reflect incomplete conversion from the acid to the salt.

F. Thermogravimetric Analysis (TGA)

TGA was carried out using a TA Instruments Model Q5000. Instrument calibration verification was performed in compliance with USP <891>, using a nickel standard. Asiatic acid and two sodium salts, AJF09,82 and AJF09,99b, were analyzed (FIGS. 10-12) The asiatic acid starting material degraded by 400° C., as evidenced in the thermogram. Thermograms obtained for both salts reflect a higher tolerance to temperature, a phenomenon often observed when a salt is formed from a compound.

G. Sodium Content Determination

Sodium content was determined by means of a Perkin Elmer AAnalyst 300 Atomic Absorption Spectrophotometer, equipped with an HGA 850 Graphite Furnace and using an oxidizing air-acetylene flame and detection at 589 nm. Standard solutions of sodium were prepared from a stock of sodium chloride at a concentration of 1000 mg/L. Typically, the analysis of sodium by this technique is performed in the presence of an alkali salt, such as cesium, to control the ionization. In this case, preliminary experiments were conducted to determine the amount of cesium (in the form of CsCl) that would be necessary to maximize sensitivity for sodium. Based on these experiments, 0.3% CsCl was used for all sample and standard preparations.

Standard Stock 1 (1000 ppm Na)

This was prepared by dissolving an accurately weighed amount of sodium chloride (2.53 g) into a 1.0 L volumetric flask and bringing to volume with deionized water after dissolution.

3% Cesium Chloride

This was prepared by dissolving an accurately weighed amount of Cesium Chloride (3 g) into a 100 mL volumetric flask and bringing to volume with deionized water after dissolution.

0.3% Cesium Chloride (Diluent)

This was prepared by dissolving an accurately weighed amount of Cesium Chloride (6 g) into 2.0 L volumetric flask and bringing to volume with deionized water after dissolution.

Diluted Stock 1 (100 ppm Na in 0.3% CsCl)

This was prepared by transferring 10.0 mL of Standard Stock 1 (1000 ppm Na) and 10.0 mL of 3% cesium chloride to a 100-mL volumetric flask with deionized water used to bring to volume.

Diluted Stock 2 (10 ppm Na in 0.3% CsCl)

This was prepared by transferring 10.0 mL of Diluted Stock 1 (100 ppm Na in 0.3% CsCl) to a 100 mL volumetric flask with 0.3% Cesium Chloride (Diluent) used to bring to volume.

Linearity of Response

The linearity of a test procedure is its ability to give test results directly proportional to the concentration of the analyte over a given range. A study of the absorption versus the corresponding sodium concentration was performed. For each set of analyses, standard solutions of NaCl were prepared by accurately transferring 2.0 mL, 3.0 mL, 4.0 mL, 5.0 mL and 6.0 mL of Diluted Stock 2 (10 ppm Na in 0.3% CsCl) into separate 50 mL volumetric flasks and bringing each to volume with Diluent to produce standards at 0.4 ppm, 0.6 ppm, 0.8 ppm, 1.0 ppm and 1.2 ppm, respectively. Each solution was read three (3) times by the instrument, and the average of the three readings was employed to generate the linearity curve (FIG. 13).

Asiatic acid sodium salts AJF09,82 and AJF09,99b were analyzed. The results are presented in Table 3.

TABLE 3

Sodium Content of Asiatic Acid Salts

| Material | Lot # | Mass of Sample (mg) | Absorption | Average Absorption | Na (ppm) from Linearity Curve | % Na in Sample |
|---|---|---|---|---|---|---|
| Asia-Na in NaOH | AJF09-99 | 3.01 | 0.125<br>0.127<br>0.130 | 0.127 | 0.77 | 5.13 |
| Asia-Na in Carbonate | AJF09,82 | 2.13 | 0.067<br>0.067<br>0.066 | 0.067 | 0.92 | 8.67 |

If there is assumed to be one molecule of sodium for each molecule of asiatic acid salt, then a content of about 4.5% sodium in the sample would be expected.

The present invention is further described by reference to the additional examples below, which are illustrative and not limiting of the invention.

Effect on Bleomycin-Induced Pulmonary Fibrosis in Rats

1. Purpose

To observe the effect of asiatic acid and asiaticoside on bleomycin-induced pulmonary fibrosis in rats, dosing was effected on the $2^{nd}$ day and the $7^{th}$ day, respectively, after the disease model was established.

2. Materials and methods

Animal: SD rats (male) weight 250-300 g from Shanghai SLACC Co. Ltd

TFG-β Kit, Human 96T ELISA kit imported by Shanghai Jingmei

TNF-α Kit, Human 96T ELISA kit imported by Shanghai Jingmei

Asiaticoside (≥92% purity)

Asiatic acid (≥98% purity)

Bleomycin for injection use from Tianjin Taihe Pharmaceutical, spec: 8 mg/Ap

Dexamethasone Shanghai Sinepharm, spec: 5 mg/Ap

3. Dosage and administration route

| | | |
|---|---|---|
| Asiatic acid | 3, 9, and 27 mg/kg | oral (p.o.) × 28 days |
| Asiaticoside | 36 mg/kg | p.o. × 28 days |
| Dexamethasone | 0.6 mg/kg | p.o. × 28 days |
| Bleomycin | 5 mg/kg | p.o. × 28 days |

4. Methods

Male SD rats, body weight 250-300 g. The animals were anesthetized with 3% seconal, laid flat and fixed onto the operating table. The necks of the animals were disinfected with alcohol and cut to expose tracheae. A needle was inserted via the space between tracheal rings centripetally, and 5 mg/kg of bleomycin was injected. The rats were kept upright and rotated, in order to keep the solution uniformly distributed in the lungs. Then the incisions were sutured.

After the rats regained consciousness, they were randomly grouped. The animals were divided into (i) a group receiving administration on the next day after establishing the model and (ii) a group receiving administration at 7 days after the model was established. Included were 27, 9, and 3 mg/kg p.o.×28 d asiatic acid groups, 0.6 mg/kg p.o.×28 d dexamethasone group, 36 mg/kg p.o.×28 d asiaticoside group, model group, and blank group. Normal saline was administered for the model and blank groups. On the 28th day after asiatic acid and asiaticoside administration, survival and weight ratio of lungs were measured; pathological examination and serological examination were performed.

TABLE 4

Mortality during experiment days 7-28

| | dosing started on $2^{nd}$ day | | | | dosing started on $7^{th}$ day | | |
|---|---|---|---|---|---|---|---|
| Group | sample number in the group | sample number on day 7 | remaining samples at the end of study | number of deaths | sample number in the group | remaining samples at the end of study | number of deaths |
| Normal | 10 | 10 | 10 | 0 | 10 | 10 | 0 |
| Asiatic acid-H | 15 | 13 | 13 | 0 | 13 | 13 | 0 |
| Asiatic acid-M | 15 | 14 | 13 | 1 | 13 | 12 | 1 |
| Asiatic acid-L | 15 | 13 | 11 | 2 | 13 | 12 | 1 |
| Asiaticoside | 15 | 14 | 12 | 2 | 13 | 11 | 2 |
| Dexamethasone | 15 | 14 | 6 | 8 | 13 | 6 | 7 |
| Model | 15 | 13 | 5 | 8 | 13 | 7 | 6 |

Effect of on lung weight index of bleomycin-induced pulmonary fibrosis in rats treated with asiatic acid Body weight and lung weight were measured after the rats were sacrificed.

Lung weight ratio=(lung weight/body weight)×100%.

The results are shown in Tables 5 and 6. In the following tables one asterisk (*) indicates a difference that is significant (P<0.05), compared with the model group; two asterisks (**) indicate a very significant difference (P<0.01).

TABLE 5

Lung weight index after 28-day administration of asiatic acid started from the second day

| Group | N | weight (g) X ± SD | lung weight (g) X ± SD | lung weight ratio (%) |
|---|---|---|---|---|
| blank control group | 10 | 438.90 ± 18.98 | 2.20 ± 0.14 | 0.50** |
| model group 5 mg/kg | 5 | 234.60 ± 47.44 | 3.37 ± 0.56 | 1.44 |
| dexamethasone group 0.6 mg/kg | 6 | 157.33 ± 16.74 | 2.06 ± 0.52 | 1.31 |
| asiaticoside group 36 mg/kg | 10 | 311.30 ± 28.76 | 2.62 ± 0.38 | 0.84** |
| asiatic acid group 3 mg/kg | 10 | 328.33 ± 31.64 | 2.74 ± 0.54 | 0.84** |
| Asiatic acid group 9 mg/kg | 10 | 316.80 ± 49.73 | 2.49 ± 0.40 | 0.78** |
| Asiatic acid group 27 mg/kg | 10 | 347.8 ± 59.3 | 2.41 ± 0.38 | 0.69** |

TABLE 6

Lung weight index after 28-day administration of asiatic acid started 7 day after model established by bleomycin

| Group | N | weight (g) X ± SD | lung weight (g) X ± SD | lung weight ratio (%) |
|---|---|---|---|---|
| Blank control group | 10 | 438.90 ± 18.98 | 2.20 ± 0.14 | 0.50** |
| model group 5 mg/kg | 7 | 248.40 ± 28.23 | 3.02 ± 0.56 | 1.22 |
| dexamethasone group 0.6 mg/kg | 6 | 179.00 ± 16.01 | 2.05 ± 0.40 | 1.14 |
| asiaticoside group 36 mg/kg | 10 | 324.60 ± 44.06 | 2.59 ± 0.33 | 0.80** |
| asiatic acid group 3 mg/kg | 10 | 317.70 ± 44.19 | 2.64 ± 0.33 | 0.83** |
| asiatic acid group 9 mg/kg | 10 | 329.30 ± 30.54 | 2.69 ± 0.53 | 0.82** |
| asiatic acid group 27 mg/kg | 10 | 343.30 ± 49.57 | 2.52 ± 0.25 | 0.73** |

As shown in Tables 5 and 6, lung weight ratio of rats in high-, middle- and low-dose asiatic acid groups, starting on $2^{nd}$ or $7^{th}$ day, was significantly lower, compared with the model group. Results from the asiaticoside group were similar to those for the asiatic acid groups. Lung weight indices in the dexamethasone group were relatively higher, probably due to a reduction in body weight caused by dexamethasone.

Serological effect of asiatic acid treatment on some cytokines in rats of bleomycin-induced pulmonary fibrosis Serum samples were prepared according to a standard protocol (centrifuged 3000 rpm, 10 minutes after collection) and were stored at −20° C. Testing was conducted in accordance with kit instructions. The results are shown in Table 7.

TABLE 7

Serological test results of asiatic acid

| Group/OD value | TFG-β ($2^{nd}$ day) X ± SD | TFG-β (7th day) X ± SD | TNF-α ($2^{nd}$ day) X ± SD | TNF-α ($7^{th}$ day) X ± SD |
|---|---|---|---|---|
| blank control group | 0.665 ± 0.137** | 0.829 ± 0.273** | 0.024 ± 0.008** | 0.053 ± 0.010** |
| model group 5 mg/kg | 1.134 ± 0.166 | 1.795 ± 0.396 | 0.066 ± 0.006 | 0.109 ± 0.031 |
| dexamethasone group 0.6 mg/kg | 0.751 ± 0.214** | 0.717 ± 0.197** | 0.073 ± 0.006 | 0.060 ± 0.006* |
| asiaticoside group 36 mg/kg | 0.670 ± 0.155** | 1.181 ± 0.364** | 0.064 ± 0.013 | 0.091 ± 0.027* |
| asiatic acid group 3 mg/kg | 0.726 ± 0.220** | 1.494 ± 0.273 | 0.055 ± 0.008* | 0.084 ± 0.018* |

TABLE 7-continued

Serological test results of asiatic acid

| Group/OD value | TFG-β ($2^{nd}$ day) X ± SD | TFG-β (7th day) X ± SD | TNF-α ($2^{nd}$ day) X ± SD | TNF-α ($7^{th}$ day) X ± SD |
|---|---|---|---|---|
| asiatic acid group 9 mg/kg | 0.642 ± 0.139** | 1.165 ± 0.412 | 0.056 ± 0.016* | 0.096 ± 0.036* |
| asiatic acid group 27 mg/kg | 0.653 ± 0.157** | 1.049 ± 0.363** | 0.050 ± 0.007** | 0.047 ± 0.013** |

Pathological analysis of the effects of asiatic acid on pulmonary fibrosis induced by bleomycin in rats The lung tissues were fixed in 10% formalin for 1 week. The tissues of the inferior lobes of the two lungs were dehydrated and dipped in paraffin, and paraffin embedding and sectioning were performed. The thickness of sections was 3-4 p.m. Routine hematoxylin-eosin (HE) staining was performed. Dual special staining of collagen fibers and elastic fibers were conducted in order to detect the degree of fibrosis. The staining of the two groups of sections was observed and the results were as follows.

Group Receiving Administration on the Next Day after Establishing Model with Bleomycin Normal Group The morphological structures of the lung tissues of animals were intact, and there was no hemorrhage, proliferation or edema. However, there was infiltration of a few inflammatory cells in the lung tissues of most of the animals. There was infiltration of a few inflammatory cells. There was serious infiltration of inflammatory cells and congestion in some local areas in some animals.

Dual staining of collagen fibers and elastic fibers showed that the alveolar septum was slightly thickened, and there was proliferation of a few fibroblasts.

Model Group

There was infiltration of inflammatory cells (mainly lymphocytes) and hyperplasia of alveolar septum in the lung tissues of animals. There was moderate to serious localized thickening in alveolar septum and there was moderate hyperplasia of fibroblasts in the thickened lesions. There was serious alveolitis, and the fibroplasia might involve the periphery area of terminal bronchioles so that there was almost no pulmonary alveolus in some areas. There was mild atrophy of pulmonary alveolus or emphysema under the pulmonary pleura.

Dual staining of collagen fibers and elastic fibers showed that there was proliferation of a great number of collagen fibers and elastic fibers in lung tissues. There was almost no pulmonary alveolus in some fields. There was hyperplasia of collagen fibers and elastic fibers in some vessel walls. The lumens turned small, and there was hyperplasia of a great deal of collagen fibers and elastic fibers around the blood vessels.

Dexamethasone Group

There was mild infiltration of inflammatory cells (mainly lymphocytes) in the lung tissues. There was infiltration of a few inflammatory cells in the pulmonary alveoli, and there was mild hyperplasia of alveolar septum. There was mild proliferation of fibroblasts, bulla formed, and there was mild pulmonary atrophy and emphysema under pulmonary pleura.

Collagen fiber and elastic fiber staining showed that there was a little proliferation of collagen fibers and elastic fibers in lung tissues.

Asiatic Administration Group

There was mild inflammation and alveolitis (mainly lymphocyte lymphocytes) in lung tissues. There was mild hyperplasia of alveolar septum, and mild pulmonary atrophy or emphysema could be found under septum. The degree and range of the above pathological changes were similar to those of dexamethasone administration group, but less serious than those of the model group.

The staining results of collagen fibers and elastic fibers were similar to those of dexamethasone administration group.

Asiatic Acid Low Dose Group

There was mild inflammation and alveolitis (mainly lymphocyte lymphocytes) in lung tissues. There was mild hyperplasia of alveolar septum, the alveolar septum was a little thickened, there was proliferation of a few fibroblasts, and mild pulmonary atrophy or emphysema could be found under septum. The degree and range of the above pathological changes were similar to those of asiaticoside group.

The staining results of collagen fibers and elastic fibers were similar to those of dexamethasone group.

Middle Dose Asiatic Acid Group

There was mild infiltration of inflammatory cells (mainly lymphocytes) in the lung tissues. The inflammation involved pulmonary alveoli, and there was mild thickening and hyperplasia of alveolar septum. There was mild proliferation of fibroblasts, and there was mild atrophy of pulmonary alveoli and emphysema under pulmonary pleura.

The collagen fiber and elastic fiber staining revealed fibroplastic proliferation, which was significantly milder than that of the model group. The range and degree in most of the rats were similar to those of the low-dose group, but in a few rats in this group the pathological changes were milder than those of the low-dose group.

Asiatic Acid High Dose Group:

There was mild infiltration of inflammatory cells (mainly lymphocytes) in the lung tissues. The inflammation involved pulmonary alveoli, and there was mild thickening of alveolar septum. There was mild proliferation of fibroblasts, and there was mild atrophy of pulmonary alveoli and emphysema under pulmonary pleura.

Collagen fiber and elastic fiber staining showed there was only a little fibroplastic proliferation, which was similar to that of the normal group in some fields. The pathological changes in this group were milder than those in the middle and low dose groups and asiaticoside group.

Group Receiving Administration at 7 Days after Establishing Model with Bleomycin The conditions of the normal group and model group were similar to those of the group receiving administration on the next day after establishing model.

Dexamethasone Group

There was mild infiltration of inflammatory cells (mainly lymphocytes) in the lung tissues. There was infiltration of a few inflammatory cells in the pulmonary alveoli, and there was mild thickening of alveolar septum. There was mild proliferation of fibroblasts, many bulla formed, and there was mild pulmonary atrophy and emphysema under pulmonary pleura. The pathological changes were significantly more serious than those of the group receiving dexamethasone on the next day after establishing model.

The collagen fiber and elastic fiber staining showed that there was fibroplasia in lung tissues, and the thickness of alveolar wall and the degree of fibroplasia were significantly more serious than those of the group receiving dexamethasone on the next day after establishing model.

The conditions of each dose group of asiaticoside and asiatic acid were similar to those of the groups receiving administration on the next day after establishing model with bleomycin.

5. Analysis

Pulmonary fibrosis induced by bleomycin is a "gold standard" model for mechanistic research on pulmonary fibrosis and, in general for discovery of anti-fibrosis and anti-inflammatory therapeutics. The biochemical and morphological changes seen in the lungs of many species after bleomycin treatment simulate those seen in humans.

The inflammatory and fibrosis pathways activated by bleomycin treatment are similar to those seen in inflammatory and fibrotic diseases, such as diabetic nephropathy (renal fibrosis). Moreover, Gauldie et al., *Proc. Am. Thorac. Soc.* 3: 696-702 (2006), have presented evidence indicating that chronic obstructive pulmonary diseases (COPD), including emphysema, depend on some of the same dysregulated pathways. Accordingly, the results of the present invention comport with a utility for therapeutic compositions, as described above, in treating diseases of inflammation and fibrosis, such as arthritis, inflammatory bowel disease, psoriasis, pulmonary fibrosis, diabetic nephropathy, and COPD.

Because pneumonia caused by bleomycin and later pulmonary fibrosis are very severe, 50-70% of the animals died in the model group. Animal deaths should be considered to be related to respiratory failure, caused by chronic inflammation and fibrosis. Dexamethasone was not able to protect rats from bleomycin-induced death. Surprisingly, asiaticoside and asiatic acid largely prevented bleomycin-induced death.

The results also show that asiatic acid can lower TNF-α and TGF-β levels, with the highest doses slightly more efficacious.

Hematoxylin-eosin staining was adopted as a regular test, and collagen fiber and elastic fiber double staining was performed, in order better to observe the anti-fibrosis effect. Pathology results demonstrate that asiatic acid was effective against bleomycin-induced pulmonary fibrosis, on a dose-response basis. Efficacy in the asiatic acid high-dose group was better than in the asiaticoside group, while the middle- and low-dose groups were similar to the asiaticoside group. Interestingly, there was a significant pathological difference between the dexamethasone group with dosing started on the $2^{nd}$ day and the $7^{th}$ day after model establishment: pulmonary fibrosis was more significantly relieved when dosing was started on the $2^{nd}$ day. This may be due to dexamethasone's exerting its anti-fibrosis effect by inhibiting inflammation. Once the early stage of inflammation has taken place, the efficacy of dexamethasone drops. Asiatic acid and asiaticoside act at both the early inflammatory stage and the later fibrosis stage; hence, efficacy did not vary as much between the groups when the compounds were administrated at the $2^{nd}$ day and $7^{th}$ day, post-insult.

Accordingly, purified asiatic acid and asiaticoside have been shown to counter the effects of bleomycin-induced inflammation and fibrosis.

Dosing started on day 7 after bleomycin treatment can affect the efficacy of dexamethasone, but it did not significantly influence the efficacy of asiatic acid or asiaticoside. This suggests that asiaticoside and asiatic acid do not just act through inhibition of inflammation, which occurs shortly after bleomycin treatment. Instead, the data support a direct inhibitory action of asiaticoside and asiatic acid on both the inflammatory and the fibrotic processes.

TABLE 8

Measured Value of Hydroxyproline in Experiment of Asiatic Acid Antagonizing Fibrosis

| | Blank control | Model control | Dexamethasone | Asiaticoside 36 mg/kg | Asiatic acid 3 mg/kg | Asiatic acid 9 mg/kg | Asiatic acid 27 mg/kg |
|---|---|---|---|---|---|---|---|
| Measured Value of Hydroxyproline in Experiment of Asiatic Acid Antagonizing Fibrosis (on $2^{nd}$ day) | | | | | | | |
| 1 | 16.35 | 35.62 | 19.86 | 28.56 | 19.57 | 28.26 | 17.64 |
| 2 | 18.65 | 29.55 | 23.31 | 28.69 | 28.21 | 15.05 | 25.36 |
| 3 | 17.11 | 28.92 | 21.69 | 19.63 | 24.03 | 29.14 | 25.18 |
| 4 | 19.25 | 24.69 | 24.63 | 25.34 | 19.66 | 28.98 | 24.36 |
| 5 | 24.36 | 29.58 | 25.36 | 28.11 | 25.61 | 27.69 | 20.19 |
| 6 | 15.36 | | 25.87 | 20.54 | 26.55 | 19.03 | 18.6 |
| 7 | 25.16 | | | 25.36 | 26.34 | 19.46 | 19.36 |
| 8 | 14.11 | | | 19.47 | 24.09 | 18.22 | 20.97 |
| 9 | 19.5 | | | 25.25 | 19.07 | 24.01 | 27.69 |
| 10 | 21.93 | | | 20.11 | 29.99 | 19.56 | 17.11 |
| X | 19.18 | 29.67 | 23.45 | 24.11 | 24.31 | 22.94 | 21.65 |
| SD | 3.70 | 3.90 | 2.32 | 3.82 | 3.80 | 5.27 | 3.71 |
| Measured Value of Hydroxyproline in Experiment of Asiatic Acid Antagonizing Fibrosis (on $7^{th}$ day) | | | | | | | |
| 1 | 18.69 | 39.66 | 25.17 | 28.19 | 20.31 | 28.19 | 19.68 |
| 2 | 25.31 | 36.97 | 27.44 | 24.36 | 27.14 | 24.39 | 19.47 |
| 3 | 19.17 | 38.07 | 25.99 | 28.17 | 28.27 | 27.98 | 20.14 |
| 4 | 16.39 | 29.00 | 29.66 | 24.69 | 26.14 | 28.36 | 24.36 |
| 5 | 19.08 | 27.08 | 28.07 | 29.1 | 28.01 | 19.36 | 27.14 |
| 6 | 17.36 | 29.11 | 27.75 | 25.11 | 29.34 | 24.64 | 24.36 |
| 7 | 19.97 | 24.03 | | 25.91 | 25.07 | 25.66 | 25.1 |
| 8 | 20.39 | | | 24.97 | 25.36 | 29.47 | 26.38 |

TABLE 8-continued

Measured Value of Hydroxyproline in Experiment of Asiatic Acid Antagonizing Fibrosis

|    | Blank control | Model control | Dexamethasone | Asiaticoside 36 mg/kg | Asiatic acid 3 mg/kg | Asiatic acid 9 mg/kg | Asiatic acid 27 mg/kg |
|----|---------------|---------------|---------------|-----------------------|----------------------|----------------------|------------------------|
| 9  | 19.99         |               |               | 29.69                 | 25.47                | 24.39                | 27.66                  |
| 10 | 23.01         |               |               | 25.55                 | 21.37                | 19.66                | 19.74                  |
| X  | 19.94         | 31.99         | 27.35         | 26.57                 | 25.65                | 25.21                | 23.40                  |
| SD | 2.60          | 6.13          | 1.59          | 2.00                  | 2.90                 | 3.52                 | 3.32                   |

TABLE 9

Type III Collagen Content - Results for Dosing with Asiatic Acid Starting Day 7
Type III collagen content (treatment starting on Day 7)

| Group | N | X ± SD |
|---|---|---|
| Asiatic acid - high dose | 10 | 0.387 ± 0.287 |
| Asiatic acid - Medium dose | 10 | 0.515 ± 0.398 |
| Asiatic acid - low dose | 10 | 0.764 ± 0.826 |
| Asiaticoside | 10 | No readout, as color reaction didn't work for this row |
| Dex | 6 | 0.518 ± 0.527 |
| Model - untreated | 5 | 1.260 ± 0.934 |
| Normal | 10 | 0.147 ± 0.045 |

What is claimed is:
1. A trometamol salt of asiatic acid.

* * * * *